United States Patent
Nosrati et al.

(10) Patent No.: US 11,211,165 B1
(45) Date of Patent: Dec. 28, 2021

(54) SMART REMOTE PATIENT MONITORING (SRPM)

(71) Applicants: Farhad David Nosrati, Tarzana, CA (US); Farzad Nosrati, Beverly Hills, CA (US)

(72) Inventors: Farhad David Nosrati, Tarzana, CA (US); Farzad Nosrati, Beverly Hills, CA (US)

(*) Notice: Subject to any disclaimer, the term of this patent is extended or adjusted under 35 U.S.C. 154(b) by 0 days.

(21) Appl. No.: 17/023,334

(22) Filed: Sep. 16, 2020

Related U.S. Application Data

(60) Provisional application No. 63/071,232, filed on Aug. 27, 2020.

(51) Int. Cl.
| | |
|---|---|
| *G06F 15/173* | (2006.01) |
| *G16H 40/67* | (2018.01) |
| *H04L 29/06* | (2006.01) |
| *H04L 29/08* | (2006.01) |
| *H04W 12/06* | (2021.01) |
| *G06F 21/62* | (2013.01) |

(52) U.S. Cl.
CPC ......... *G16H 40/67* (2018.01); *G06F 21/6245* (2013.01); *H04L 63/0861* (2013.01); *H04L 67/22* (2013.01); *H04W 12/06* (2013.01)

(58) Field of Classification Search
None
See application file for complete search history.

(56) References Cited

U.S. PATENT DOCUMENTS

2020/0260955 A1* 8/2020 Cronin .................. A61B 5/746

OTHER PUBLICATIONS

Medbot: Conversational Artificial Intelligence Powered Chatbot for Delivering Tele-Health after COVID-19, Urmil Bharti, et al., Publication Date: Jun. 1, 2020, Electronic Publication Date: Jul. 9, 2020, 2020 5th International Conference on Communication and Electronics Systems (ICCES) (pp. 870-875).*

* cited by examiner

*Primary Examiner* — Brian Whipple
*Assistant Examiner* — Gregory P Tolchinsky

(57) ABSTRACT

Systems and methods for improving Remote Patient Monitoring by utilizing a plurality of physiological test devices with built-in hardware, software and wireless connectivity redundancy mechanisms to help ensure successful remote patient monitoring in the event of hardware and software failures as well as wireless communication disruption and down-time. A time-delayed method for the transmission of the acquired physiological parameters are utilized for reliable delivery of patient test data to remote server in the event of disruption in wireless communication services. Additionally, Artificial Intelligent (AI) Avatar Virtual Assistant with passive "Check My Status' monitoring is utilized to provide a multilayer testing mechanism within remote patient monitoring by interactively communicating with the patient via voice using Speech To Text (STT), Text To Speech (TTS) and Natural Language Processing (NLP).

9 Claims, 16 Drawing Sheets

RPM App and Physician Portal- Artificial Intelligence Avatar Assistant Multi-dimensional Testing

FIG. 1  RPM APP - Primary RPM Mobile Device Failure

FIG. 2      RPM APP - Primary Medical Device Failure

FIG. 3      RPM Backend Server - Primary Backend Server Failure

FIG. 4      RPM Physician Portal- Primary Physician Portal Failure

RPM APP - Primary RPM App Failure

FIG. 6 RPM APP – Delayed Wireless Transmission

RPM Physician Portal- Multi-Layer Permission and Role Assignment

RPM App and Physician Portal- Artificial Intelligence Avatar Assistant

RPM App and Physician Portal- Artificial Intelligence Avatar Assistant Multi-dimensional Testing FIG. 10 — RPM App - Artificial Intelligence Avatar Assistant "Check My Status" Process RPM App – One-Touch On-Screen Emergency Response Button RPM App - Out of Range Test Results with Color-Coded Notification Process FIG. 13  RPM App - Out of Range Test Results with Color-coded and ALERT Notification Process FIG. 14                                RPM APP – Initial Setup RPM App – Secure Remote Patient Monitoring Process RPM APP – Multi-Healthcare Provider Remote Patient Monitoring

SMART REMOTE PATIENT MONITORING (SRPM)

CROSS-REFERENCE TO RELATED APPLICATIONS

This application takes priority from provisional application Ser. No. 63/071,232 filed on Aug. 27, 2020.

FIELD OF THE INVENTION

Systems and methods for improving Remote Patient Monitoring comprising software Application program (APP) residing on a tablet or mobile device; one or more patient monitoring equipment for use at a patient location; configured to receive and collect one or more patient physiological parameters of a patient and transmit the collected patient physiological parameters wirelessly to a remote server while providing built-in hardware, software and wireless connectivity redundancy mechanisms to help ensure successful remote patient monitoring in the event of hardware and software failures as well as wireless communication disruption and down-time. A time-delayed method for the transmission of the acquired physiological parameters are utilized for reliable delivery of patient test data to remote server in the event of disruption in wireless communication services. Additionally, Artificial Intelligent (AI) Avatar Virtual Assistant with passive "Check My Status' monitoring is utilized to provide a multilayer testing mechanism within remote patient monitoring by interactively communicating with the patient via voice using Speech To Text (STT), Text To Speech (TTS) and Natural Language Processing (NLP).

BACKGROUND OF THE INVENTION

Remote Patient Monitoring systems enable healthcare providers to remotely utilize wireless medical diagnostic devices. The user will take one or more tests such as his or her temperature and weight and manually enter that information into the Remote Patient Monitoring (RPM) system.

Prior Art RPM system further comprise of an App that gets loaded on a tablet or mobile device of the patient to collect patient the collected test data to the remote server for healthcare provider reviewing and monitoring.

Yet, more advanced prior art remote patient monitoring systems enable healthcare providers to remotely utilize wireless medical diagnostic devices such as a blood pressure monitor, thermometer SpO2 and Weight Scale. The tablet or mobile device captures the user test data either manually or wirelessly pairs with and connects to one or more medical diagnostic devices, and acts as a remote control to activate the device, conduct one or more tests on the said patient and collect physiological parameters from one or more devices.

The tablet or mobile device wirelessly pairs with and connects to one or more medical diagnostic devices, and acts as a remote control to activate the device, conduct one or more tests on the said patient and collect physiological parameters from one or more devices.

The tablet or mobile device, collects the patient physiological parameters wirelessly from one or more medical diagnostic device and transfers that information to a remote backend server for storage as well as access by the healthcare providers.

Healthcare providers can then utilize a web portal to access and view the remotely transmitted patient physiological parameters. The web portal will provide a User Interface for the healthcare provider to view patient data in tabular text format as well as in charts and graphs.

Healthcare provider can further utilize the portal to conduct audio and video consultation with the patient using his or her tablet and mobile device.

Deficiencies and Short Comings of Prior Art RPM number of deficiencies and short comings are clearly apparent in current RPM systems.

Prior Art RPM App and Physician Portals provide no solution to manage data transmission during wireless signal disruption. Intermittent wireless communication can jeopardize reliability of transmission for physiological parameters being obtained from patient using medical diagnostic devices.

Prior Art RPM Apps further lack Ability to simultaneously acquire physiological parameters thru both connected and non-connected (manual entry) medical diagnostic device.

Prior Art RPM Apps lack interactive Message Center.

Prior Art RPM Physician Portals lack interactive Message Center.

Prior Art RPM Apps lack the ability for patient to send messages to health care provider thru the RPM App and receive messages and notifications.

Prior Art RPM Apps lack Artificial Intelligence (AI) Avatar Virtual Assistant and therefore LACK the ability of supporting
  a) Communicating via STT and TTS with patient
  b) Guiding the patient on using medical device
  c) Utilizing NLP to understand the patient
  d) Supporting Artificial Intelligent Avatar Virtual Assistant to interactively speak with the patient while he or she takes the tests, in order to collect critical input from patient during the testing process and to convert the voice patient conversation to Text using STT technology and wirelessly transmitting that information to the backend server so that the healthcare provider can then read the text script of the conversation or utilize TTS technology to hear the inputted conversation from patient during the test.

Prior Art Physician Portals further LACKS dynamic multi-layer assignment of permissions and roles.

Prior art RPM Apps further LACK an on-screen Emergency Response button capability to reach emergency personnel before, during or after the test process.

Prior art RPM Apps further LACK the ability to provide integration with Wireless Personal Emergency Response button Prior art RPM Apps further LACK the ability to provide support for passive safety feature of "Check My Status"

BRIEF DESCRIPTION OF NOVELTIES OF PRESENT INVENTION

Redundancy and Alternative Backups
a. Mirroring RPM App
b. Secondary Tablet or Mobile Device
c. Alternate Medical Diagnostic Devices
d. Alternate Backend Mirror Server
e. Alternate Physician Portal Physician Portal Novelties
a. Multi-layer Permission and Role Assignment
b. Artificial Intelligence (AI) Avatar Virtual Assistant
c. AI Avatar utilizing Speech To text (STT) and Text To Speech (TTS) to interactively communicate with healthcare provider thru the physician portal d. AI Avatar utilizing Natural Language Processing (NLP) technology to understand the interactive voice communication with healthcare provider thru the physician portal
e. AI Avatar to help analyze and diagnose patient physiological parameters
f. RPM Message Center utilizing AI Avatar Virtual Assistant, STT, TTS and NLP RPM APP
a. Artificial Intelligence (AI) Avatar Virtual Assistant
b. AI Avatar Virtual Assistant utilizing Speech To Text (STT) and Text To Speech (TTS) in order to interactively communicate with patient via voice
c. AI Avatar Virtual Assistant utilizing Natural Language Processing (NLP) technology to understand the interactive voice communication with patient
d. AI Avatar Virtual Assistant to provide symptom checker process thru a series of interactive questioner
e. AI Avatar Virtual Assistant to triage the patient physiological parameters
f. Multi-dimensional RPM Testing method—AI Avatar Virtual Assistant to conduct voice communication with patient before, during and after the testing process and convert patient comments, concerns and inputs to Text and wirelessly transmit to backend server for health care provider to view
g. Wireless physiological parameters transmission recovery after a signal loss or down wireless network condition.
h. Out-Of-Range test result reporting
i. RPM App Message Center utilizing AI Avatar Virtual Assistant, STT, TTS and NLP
j. SOS Emergency On-Screen button
k. Personal Emergency Response System (PERS) integration and support RPM Security
Authenticated video consultation sessions utilizing:
  Facial recognition of patient
  Fingerprint authentication
  Retina authentication
  Two-factor authentication RPM Wearable Devices
Monitor remotely using wearable devices including watches, wristbands, patches halter monitors.
Devices live transmit data packets to backend server
Devices accommodate pre-defined safety thresholds to help alert healthcare providers, caregivers and first responders if emergency arises.

Healthcare Provider Sharing
Enable multiple providers to provide remote healthcare to patients.

One-touch on-screen Emergency Response button—to contact emergency personnel and first responders before, during or after the test process Wireless Personal Emergency Response Button integration, enabling patients to press a button on a PERS they may carry on their person to signal the present invention RPM App and mobile device to contact emergency personnel and first responders before, during or after the test process "Check My Status" passive monitoring system for the patients by providing an Artificial Intelligence (AI) avatar to periodically check on patient well-being.

DETAIL DESCRIPTION OF NOVELTIES OF PRESENT INVENTION

Present invention relates to a systems and methods for improving Remote Patient Monitoring. Among related novelties and benefits of the present invention, Smart Remote Patient Monitoring (SRPM) are:

1. Redundancy and Alternative Backups

Mirroring RPM App—Prior art RPM system comprise of an App that gets loaded on a tablet or mobile device of the patient, that communicates with one or more wireless medical diagnostic devices to conduct a test and acquire information and related data on patient's health condition. There are no redundancies built into any Prior Art RPM Apps. The present invention, Smart Remote Patient Monitoring (SRPM) system provides a clear advantage and novel redundancy capability of a Secondary "Mirroring App" that gets loaded and installed on patient tablet or mobile device. The mirroring App runs in the background as a "service" and continuously monitors the state of the primary RPM App installed on patient tablet or mobile device. In the event the primary RPM App is not responding, frozen or locked up, the secondary Mirroring App will load itself to the front and take over the RPM process by communicating with wireless medical devices, collecting physiological parameters from patient thru the said devices and transmitting that information to the backend server for healthcare provider access and viewing Secondary Tablet or Mobile Device—The primary tablet or mobile device pairs with and connects wirelessly to the medical diagnostic devices, and acts as a remote control to activate the devices, conduct one or more tests on the said patient and collect physiological parameters from one or more devices. The present invention, Smart Remote Patient Monitoring (SRPM) system provides a clear advantage and novel redundancy capability thru the use of a Secondary mobile device that can remotely be activated to perform all RPM functionality of the patient primary mobile device. In the event the primary tablet or mobile device exhibits a hardware, software or connectivity issue or runs out of battery and as result fails to perform the required RPM tasks, the secondary mobile device can be remotely selected and activated to carry-on the required RPM functionality and tasks of the primary mobile device. In such cases, the secondary mobile device which contains all capabilities of the primary mobile device, including the primary RPM App as well as the Secondary Mirroring App, pairs with and connects to the wireless medical devices, collects physiological parameters from patient thru the said devices and transmits that information to the backend server for healthcare provider access and viewing.

Alternate Medical Diagnostic Devices—The present invention, Smart Remote Patient Monitoring (SRPM) system provides a clear advantage and novel redundancy capability of supporting the use of an alternate duplicate medical diagnostic device for each of the primary medical devices being used for the RPM application. In the event the primary medical diagnostic device exhibits a hardware, software or connectivity issue or runs out of battery and as result fails to perform the required medical diagnostic test, the alternate duplicate medical diagnostic device is then automatically activated and connected to the mobile device to perform the required test and acquire the physiological parameters to be transmitted to the backend server via the mobile device for healthcare provider access and viewing.

Alternate Backend Mirror Server—The present invention, Smart Remote Patient Monitoring (SRPM) system provides a clear advantage and novel redundancy capability of supporting the use of an alternate backend mirror server for directing the health provider to access and view patient physiological date that was remotely acquired using the medical diagnostic devices utilizing the RPM App on patient tablet for mobile device. With the present invention SRPM, acquired physiological parameters thru the medical diagnostic devices are wirelessly transmitted to one or more backend "mirror server" simultaneously. In the event the primary backend server or its associated physician portal becomes inaccessible, the current SRPM automatically switches to the alternate backend mirror server.

Alternate Physician Portal—The present invention, Smart Remote Patient Monitoring (SRPM) system provides a clear advantage and novel redundancy capability of supporting the use of an alternate physician portal for directing the health provider to access and view patient physiological date that was remotely acquired using the medical diagnostic devices utilizing the RPM App on patient tablet for mobile device. With the present invention SRPM, acquired physiological parameters thru the medical diagnostic devices are wirelessly transmitted to one or more backend "mirror server" simultaneously. A secondary physician portal allows the healthcare provider to access and view the patient data received by the secondary backend mirror server. In the event the primary backend server or its associated physician portal becomes inaccessible, the current SRPM automatically redirects the healthcare provider to the secondary portal linked to the secondary backend mirror server to access and view patient physiological parameters.

2. Physician Portal

Multi-layer Permission and Role Assignment—The present invention, Smart Remote Patient Monitoring (SRPM) system provides a clear advantage and novel Physician Portal capable of assigning multiple layers of roles and permissions to the healthcare providers utilizing the physician portal to access patient physiological information acquired remotely thru the use of one or more medical diagnostic device, thru the use of the RPM App residing on patient tablet or mobile device. The present SRPM system introduces a novel multi-layer "role" assignment concept whereas in a primary layer, one or more roles can be created and assigned to various healthcare providers accessing patient data thru the physician portal. In a secondary layer, plurality of permissions and access levels can then be associated and assigned to each of the above mentioned roles. The scope of each permission and its access level can further be modified to become more restricted or less restricted thru a $3^{rd}$ role and permission assignment layer. The innovative multi-layer approach provides an extremely flexible approach to acquiring access by each healthcare provider to patient data.

Artificial Intelligence (AI) Avatar Virtual Assistant—It is another novel object of the present invention, Smart Remote Patient Monitoring (SRPM) system to utilize Artificial Intelligence (AI) to assist with healthcare provider's interactive communications and assist the healthcare provider with access with the physician portal. The above mentioned AI further comprise of a Virtual Assistant.

It is yet another novel object of the present invention to have the Artificial Intelligence (AI) Virtual Assistant utilizing Text To Speech (TTS) and Speech To Text (STT) technologies to conduct interactive voice communicate with the healthcare Providers accessing the physician portal.

It is yet another novel object of the present invention to utilize Natural Language Processing (NLP) technology.

It is another novel object of the present invention to enable the AI Avatar Assistance to understand the interactive conversation between the AI Avatar Virtual Assistant and the healthcare provider using the above mentioned NLP.

It is another novel object of the present invention for the AI Avatar Virtual Assistant to analyze patient physiological parameters remotely acquired thru the use of the medical diagnostic devices. Artificial Intelligence (AI) Avatar Assist may utilize the above mentioned TTS, STT and NLP technologies to help remotely triage the patient thru audio and video devices and conduct a symptom checker process.

Message Center—It is yet another novel object of the present invention to support a live message center on the physician portal, to provide live interactive messaging between the healthcare provider thru the portal with the patient thru his or tablet or mobile device.

It is another object of the present invention to utilize the Artificial Intelligence (AI) Virtual Assistant in the above mentioned message center.

It is another object of the present invention to enable the Artificial Intelligence (AI) Virtual Assistant in the above mentioned message center to utilize Speech To Text (STT) technology to enable the healthcare provider to speak his or her messages to be translated to text and directed to the patient's tablet or mobile device.

It is further object of the present invention to enable (AI) Virtual Assistant to utilize Text To Speech (TTS) to speak the incoming text messages from the patients for the healthcare provider.

3. APP

Artificial Intelligence (AI) Avatar Virtual Assistant—The present invention, Smart Remote Patient Monitoring (SRPM) system further comprise of a novel RPM App that gets loaded on a tablet or mobile device of the patient, that communicates with one or more wireless medical diagnostic devices to conduct a test and acquire information data on patient's health condition.

It is a novel object of the RPM App to utilize Artificial Intelligence (AI) Avatar Assist to interactively communicate with the patient and assist him or her with accessing and operating the medical diagnostic devices to perform one or more tests.

It is yet another novel object of the present invention to have the Artificial Intelligence (AI) Virtual Assistant utilizing Text To Speech (TTS) and Speech To Text (STT) technologies to conduct interactive voice communicate with the patient before, during and after the test process.

It is yet another novel object of the present invention to utilize Natural Language Processing (NLP) technology.

It is another novel object of the present invention to enable the AI Avatar Assistance to understand the interactive conversation between the AI Avatar Virtual Assistant and the patient using the above mentioned NLP.

It is another novel object of the present invention for the AI Avatar Virtual Assistant to analyze patient physiological parameters acquired thru the use of the medical diagnostic devices. Artificial Intelligence (AI) Avatar Assist may utilize the above mentioned TTS, STT and NLP technologies to help triage the patient and conduct a symptom checker process.

Multi-Dimensional RPM Testing Method—It is a novel object of the present invention Smart Remote Patient Monitoring (SRPM) to engage in interactive voice communication between the Avatar Virtual Assistant and the patient before, during and after the testing process. This will enable the patient to speak interactively with Avatar Assist and describe his or her symptoms, condition and concerns during the RPM testing process, as he or she might typically do during an in-person office visit. The Avatar Assist can then utilize Speech To Text (STT) technology to convert the patient's spoken words into text and accompany that information along with the physiological parameters obtained thru the use of the medical diagnostic devices.

This novel approach during the Remote Patient Monitoring (RPM) process provides an additional dimension of information and insight into the patient condition.

Downtime Wireless Connectivity Recovery Mode—The present invention, Smart Remote Patient Monitoring (SRPM) system provides a clear advantage of supporting a novel time-delay transmission of patient physiological parameters in the event of wireless communication failure or wireless network downtime. The tablet or mobile device using the SPRM App, interfaces with one or more medical diagnostic devices and acquires the patient physiological parameters and attempts to transmit that information to the backend for healthcare provider's access and viewing thru the SRPM Physician portal. In the event that the physiological parameters packets cannot be transmitted following the diagnostic test, the said data packets will be stored on the mobile devices non-volatile memory. SRPM App then continuously makes additional attempts to transmit the data packets, until successful wireless communication is achieved.

Out-Of-Range Test Results Reporting—It is yet another a novel object of the present invention Smart Remote Patient Monitoring (SRPM) to have the RPM App support a user programmable of in-range and out-of-range test results. In the patient physiological test result data is out of range, then urgent notification with color-coded designation will be transmitted to the backend server for healthcare provider viewing. In addition, RPM App can send the above mentioned urgent notifications directly to family members, care givers, emergency respond team and first responders.

Message Center—It is yet another novel object of the present invention to support a live message center thru the RPM APP to provide live interactive messaging between the patient and healthcare provider.

It is another object of the present invention to utilize the Artificial Intelligence (AI) Virtual Assistant in the above mentioned message center.

It is another object of the present invention to enable the Artificial Intelligence (AI) Virtual Assistant in the above mentioned message center to utilize Speech To Text (STT) technologies to enable the healthcare provider to speak his or her messages to be translated to text and directed to the patient tablet or mobile device.

It is further object of the present invention to enable (AI) Virtual Assistant to utilize Text To Speech (TTS) to speak the incoming text messages from the patients for the healthcare provider.

One-Touch On-Screen Emergency Response Button—It is yet another novel object of the present invention to support a one-touch on-screen emergency response button thru the RPM APP to provide access to emergency personnel and first responders before, during or after the testing process.

It is yet another novel object of the present invention to provide support for wireless Personal Emergency Response Button. The said wireless device can be carried by the patient and in case of a fall, or other emergencies, the patient can activate the emergency button on the said device, notifying the RPM App of the request for help. The RPM App can then utilize the mobile device wireless connectivity to initiate stress calls to emergency personnel, first responders, caregivers and family members.

4. RPM—Security and Patient Authentication

It is yet another novel object of the present invention SRPM to provide Authenticated video consultation sessions with healthcare providers utilizing secure biometrics technologies.

Current invention, SRPM utilizes Facial Recognition technology to authenticated and validate the patient prior to, during and after the remote patient monitoring (RPM) consultation session. Prior Art RPM solutions lack the ability to securely authenticate the patients being monitored remotely.

Current invention, SRPM further utilizes Biometrics fingerprint scanning technology to authenticated and validate the patient upon initiating the remote patient monitoring (RPM) consultation session to ensure the healthcare provider consultation is performed with the valid person.

Current invention, SRPM further utilizes Biometrics retina scanning technology to authenticated and validate the patient upon initiating the remote patient monitoring (RPM) consultation session to ensure the healthcare provider consultation is performed with the valid person.

Current invention, SRPM further utilizes dual-factor authentication to authenticated and validate the patient upon initiating the remote patient monitoring (RPM) consultation session to ensure the healthcare provider consultation is performed with the valid person.

5. RPM—Wearable Devices

Current invention, SRPM further utilizes wearable devices including but not limited to Smart Watches and Smart Wristbands to continuously monitor a patient and wirelessly transmit her vital signs and other physiological parameters to a remote server for healthcare provider's viewing and monitoring. The above mentioned wearable devices will utilize user programmable test threshold values to accommodate pre-defined safety thresholds to help alert healthcare providers, caregivers and first responders if emergency arises.

6. RPM—Healthcare Provider Sharing

Among novelties of the current invention, SRPM is providing the unique capabilities to allow plurality of healthcare providers to remotely monitor a patient.

Prior art RPM Apps further LACK the SOS button capability to reach emergency personnel before, during or after the test process.

One-touch on-screen Emergency Response button—to contact emergency personnel and first responders before, during or after the test process Wireless Personal Emergency Response button integration, enabling patients to press a button on a wireless personal response device such as FOB that they may carry on their person to signal the present invention RPM App and mobile device to contact emergency personnel and first responders before, during or after the test process "Check My Status" feature providing a 24/7 passive monitoring system for the patients by providing an Artificial Intelligence (AI) avatar to periodically check on patient well-being and have the patient touch the screen or speak to the AI Avatar to confirm their well-being and safety.

EXAMPLES

EXAMPLE-1: Secondary SRPM App—In one embodiment of the present invention Secure Remote Patient Monitoring (SRPM), during the initial installation and setup of the SRPM, the primary Secure Remote Patient Monitoring (SRPM) Software App is loaded and installed on the patient tablet or mobile device. A secondary SRPM App is then loaded and installed on the user tablet or mobile device and runs as a background service. The remote monitoring equipment are then wirelessly paired with and connected to the tablet or mobile device. The primary App interacts with the patient and activates the remote medical equipment to acquire patient physiological parameters and upload the acquired information to the backend to be viewed by the healthcare provider using the SRPM Physician Portal. In the event that primary App freezes, crashes or fails to establish connectivity with remote monitoring equipment's to collect patient physiological parameters, the secondary SRPM App will load to the front and take over the primary SRPM App's responsibilities by interacting with the patient and communicating with the remote monitoring equipment's to acquire patient physiological parameters and parameters and upload the acquired information to the backend to be viewed by the healthcare provider using the SRPM Physician Portal.

invention Secure Remote Patient Monitoring (SRPM), during the initial installation and setup of the primary and secondary Remote Patient Monitoring (SRPM) Software App on the patient tablet or mobile device. Following that, the Primary and Secondary SRPM Apps are also loaded on a secondary tablet or mobile device. The remote monitoring equipment are then wirelessly paired with and connected to the secondary tablet or mobile device. The backend server remotely communicates with both primary and secondary tablets thru proprietor software API commands to track their performances and ensure both tablets are functioning as required. In the event that primary tablet or mobile device exhibits a hardware, software or connectivity issue or runs out of battery and as result fails to perform the required RPM tasks, the backend serve reactivates the primary tablet or mobile device to communicate with the wireless remote patient monitoring equipment and acquire the patient physiological parameters and upload the acquired information to the backend to be viewed by the healthcare provider using the SRPM Physician Portal.

EXAMPLE-3: Alternate/Secondary medical equipment—In yet another embodiment of the present invention Secure Remote Patient Monitoring (SRPM), during the initial installation and setup process, once the remote monitoring equipment are wirelessly paired with and connected to the patient tablet or mobile device, a secondary alternative set of remote patient monitoring equipment are then wirelessly paired with and connected to the patient tablet or mobile device. In the event that the primary remote monitoring equipment fail to acquire patient physiological parameters, the SRPM App will reconnect to the secondary alternative remote monitoring equipment and acquire patient physiological parameters and upload the acquired information to the backend to be viewed by the healthcare provider using the SRPM Physician Portal.

EXAMPLE-4: Alternate/Secondary backend server—Yet another embodiment of the present invention Secure Remote Patient Monitoring (SRPM), comprises of a secondary mirror backend server, capable of communicating with patient tablets or mobile devices using a proprietor APP commands. In the event that the primary backend server fails to communicate with patient tablet or mobile device and is unable to access the patient physiological parameters acquired by the remote patient monitoring equipment, the second mirroring backend server is then reactivated to take over and perform the required tasks.

EXAMPLE-5: Alternate/Secondary physician portal—Yet another embodiment of the present invention Secure Remote Patient Monitoring (SRPM), comprises of a secondary physician web-portal. Healthcare providers access the physician web-portal to view patient physiological parameters acquired by the wireless remote monitoring equipment and uploaded to the backend server using the patient tablet or mobile device. In the event that the primary physician web-portal is not accessible, the backend server will provide a web link to the secondary physician web-portal and redirect the healthcare provider to the said secondary physician portal to access patient physiological parameters.

EXAMPLE-6: Multi-layer permission and role assignment—Yet another embodiment of the present invention Secure Remote Patient Monitoring (SRPM), comprises a novel method of creating flexible roles for healthcare providers and their staff accessing the physician web portal to view patient physiological parameters, while assigning independent access permissions to each designated role. As example, "receptionist" role maybe assigned to a staff member with the access permissions limited to patient profile and appointment schedule, while an "accountant" role maybe assigned to a different staff member with permission access to patient profile and billing information. Finally, "Office Administrator" role maybe assigned to yet another staff member with full access permission to all aspects of the SRPM thru the physician portal.

EXAMPLE-7: Artificial Intelligence (AI) Avatar Virtual Assistant in SRPM Portal—SRPM web-based physician portal utilizes an Artificial Intelligence (AI) Avatar virtual assistant. The Avatar utilizes Text To Speech (TTS) to convert the received information on each patient into speech and share that information with the healthcare provider. The healthcare provider can then talk back to the Avatar with his comments, findings and the results of his or her analysis. The Avatar further utilizes Natural Language Processing (NLP) to understand the healthcare provider's comments and questions and provide further details if needed. The Avatar can then utilize Speech To Text (STT) to convert the healthcare providers voice input into text information to file in patient's records or transmit back to the patient tablet or mobile device for his or her viewing.

EXAMPLE-8: Artificial Intelligence (AI) Avatar Virtual Assistant in SRPM App—SRPM mobile device App utilizes an Artificial Intelligence (AI) Avatar virtual assistant. The Avatar utilizes Text To Speech (TTS) to convert the received information from physician portal into speech and share that information with the patient via interactive voice. The patient meanwhile can talk with the Avatar and provide valuable information on his state of wellbeing. The Avatar further utilizes Natural Language Processing (NLP) to understand the patient conversation, questions and comments and provide further details if needed. The Avatar can then utilize Speech To Text (STT) to convert the patient's voice conversation into text information to upload into the physician portal for healthcare providers viewing. The interactive Avatar virtual assistant further enabled the patient to describe his state of well-being prior to, during and after each test via interactive voice communication with the avatar. Avatar then converts the obtained information from patient into text and uploads the converted information along with the acquired physiological parameters from remote monitoring equipment to the physician portal for healthcare providers viewing.

EXAMPLE-9: Message Center thru Avatar, STT, TTS and NLP—The SRPM further comprises a Message Center that utilizes the Artificial Intelligence (AI) Avatar virtual assistant to manage the incoming and outgoing messages between the patient and his or her healthcare provider. Using Speech To text (STT) and Text To Speech (TTS) and Natural language Processing (NLP) technologies, the Avatar interactively communicates with both the patient thru the SRPM mobile App as well as with the healthcare provider thru the Physician portal. The avatar converts the voice conversations into text information and shares the information thru the backend server and the physician portal.

EXAMPLE-10: Downtime Wireless connectivity/Delayed Transmission recovery mode in SRPM App—Once the patient physiological parameters are acquired using the remote monitoring equipment, the SRPM mobile device App then attempts to transmit that information remotely to the backend server to be viewed by the healthcare provider using the physician portal. In the event that wireless network connectivity is intermittent or unviable, the SRPM mobile App stores the acquired physiological parameters in the tablet or mobile devices internal non-volatile memory. The SRPM mobile App then continuously monitors the state of the wireless network, and once the network becomes available, SRPM mobile App transmits the patient physiological data along with the actual date and time stamp when patient physiological parameters were acquired to the backend server for healthcare provider viewing thru the physician web portal.

EXAMPLE-11: Tri-Level physiological parameters/Color-coded Notifications in SRPM App—The SRPM further comprises a set of programmable physiological filters for each patient physiological parameters obtained thru the remote monitoring equipment. The healthcare provider can then customize the above mentioned physiological filters for each individual patient remotely thru the physician web portal and download the customized filters to the patient tablet or mobile device. The healthcare provider can further customize the above mentioned physiological filters for each individual patient using the SRPM mobile App directly on patient tablet or mobile device. The SRPM mobile device App utilizes these programmable filters to determine if the obtained patient physiological parameters are a) in-range, b) abnormal or c) out-of-range. A different color code is then associated with each of the above three patient physiologic parameter groups and uploaded to the backend server for viewing by the healthcare provider thru the physician web portal.

EXAMPLE-12: Tri-Level physiological parameters/Alert notifications in SRPM App—The SRPM further comprises a set of customized alert notification levels associated with each of the above mentioned programmable physiological filters associated with each patient physiological parameters obtained thru the remote monitoring equipment. The SRPM mobile device App utilizes the programmable filters to determine if the obtained patient physiological parameters are a) in-range, b) abnormal or c) out-of-range. An alert notification in form of a text message, email or a voice call is then generated to one or more recipients based on the determined level of the alert.

EXAMPLE-13: On-screen 1-touch SOS button in SRPM App—The SRPM mobile App further comprises an emergency response SOS button on the tablet or mobile device screen. The patient can send out alert notifications prior to, during or after each physiological test by simply touching the SOS button on his or her tablet or mobile device. The SRPM mobile App can be configured to send the alert notifications in plurality of methods including Text message, email and phone calls.

EXAMPLE-14 Security Biometrics in SRPM App—The SRPM mobile App further comprises biometrics login and verification to authenticate each patient. The biometric authentication ensures secure login to the SRPM mobile App. The biometric authentication further validates the patient being monitored thru the remote monitoring equipment. The SRPM secure biometric verification and authentication includes fingerprint scan, retina scan, facial recognition and voice recognition.

EXAMPLE-15: Security 2-factor authentication in SRPM App—The SRPM mobile App further comprises 2-factor authentication which is used to a) provide secure login and b) validates the patient being monitored thru the remote monitoring equipment. As an example, the patient may be required to use an RFID card or a wireless dongle displaying a secondary password in addition to his or her login credentials. Another example would be for patient to authenticate thru an email in addition to his or her login credentials.

EXAMPLE-16: Check My Status Passive Monitoring (CMS) in SRPM App—The SRPM mobile App further comprises a "Check My Status" passive monitoring capability. Using a pre-programmed schedule, the SRPM App will initiate a CSM notification on the patient tablet or mobile device. The CMS schedule may be programmed by the healthcare provider remotely thru the physician web-portal and downloaded to the patient tablet or mobile device. The above CMS schedule may also be programmed by the healthcare provider, caregiver or the patient locally on the patient tablet or mobile device thru the SRPM mobile App. In one configuration, the CSM notification comprises of an audio alarm or message notifying the patient to acknowledge their well-being by tapping the tablet or mobile device screen. In yet another configuration, the CSM notification comprises of messages displayed on the tablet or mobile device screen, notifying the patient to acknowledge their well-being by tapping the tablet or mobile device screen.

EXAMPLE-17: SRPM Wearable Devices—In one embodiment, the SRPM utilizes wearable devices including but not limited to smart watches and bracelets. The wearable devices acquire patient physiological parameters and transmit them wirelessly to the backend server for the healthcare provider viewing thru the SRPM physician web-portal.

EXAMPLE-18: SRPM Integration of Personal Emergency Response System (PERS)—The SRPM mobile App further comprises the integration of wireless Personal Emergency Response System (PERS). The patient can utilize the wireless PERS to remotely communicate with the SRPM mobile App on patient tablet or mobile device and send alert notifications to his or her healthcare provider, emergency first responders, caregiver and family members.

BRIEF DESCRIPTION OF DRAWINGS

The aforementioned objects and advantages of the present invention, as well as additional objects and advantages thereof, will be more fully understood herein after as a result of a detailed description of a preferred embodiment when taken in conjunction with the following drawings, which are the purpose of illustration only and not limitation, and in which.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope, and contemplation of the present invention.

It should be noted that references to "an," "one," or "various" embodiments in this disclosure are not necessarily to the same embodiment, and such references contemplate more than one embodiment.

The present invention disclosed herein and illustrated in FIGS. 1 through 31 is the present invention Collection of Digital Health Hubs (HH) with Artificial Intelligence to autonomously communicate with each other to create a fully automated digital health social network.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the term "Computing Device"" includes a desktop, laptop or tablet computer, as well as a mobile device.

As used herein the term "User" includes a general user.

As used herein the term "User" includes a patient seeking healthcare services.

As used herein the term "User" includes a person seeking legal advice from a legal counsel or an attorney.

As used herein the term "provider" includes a healthcare service provider.

As used herein the term "provider" includes a legal service provider.

Figure 1:
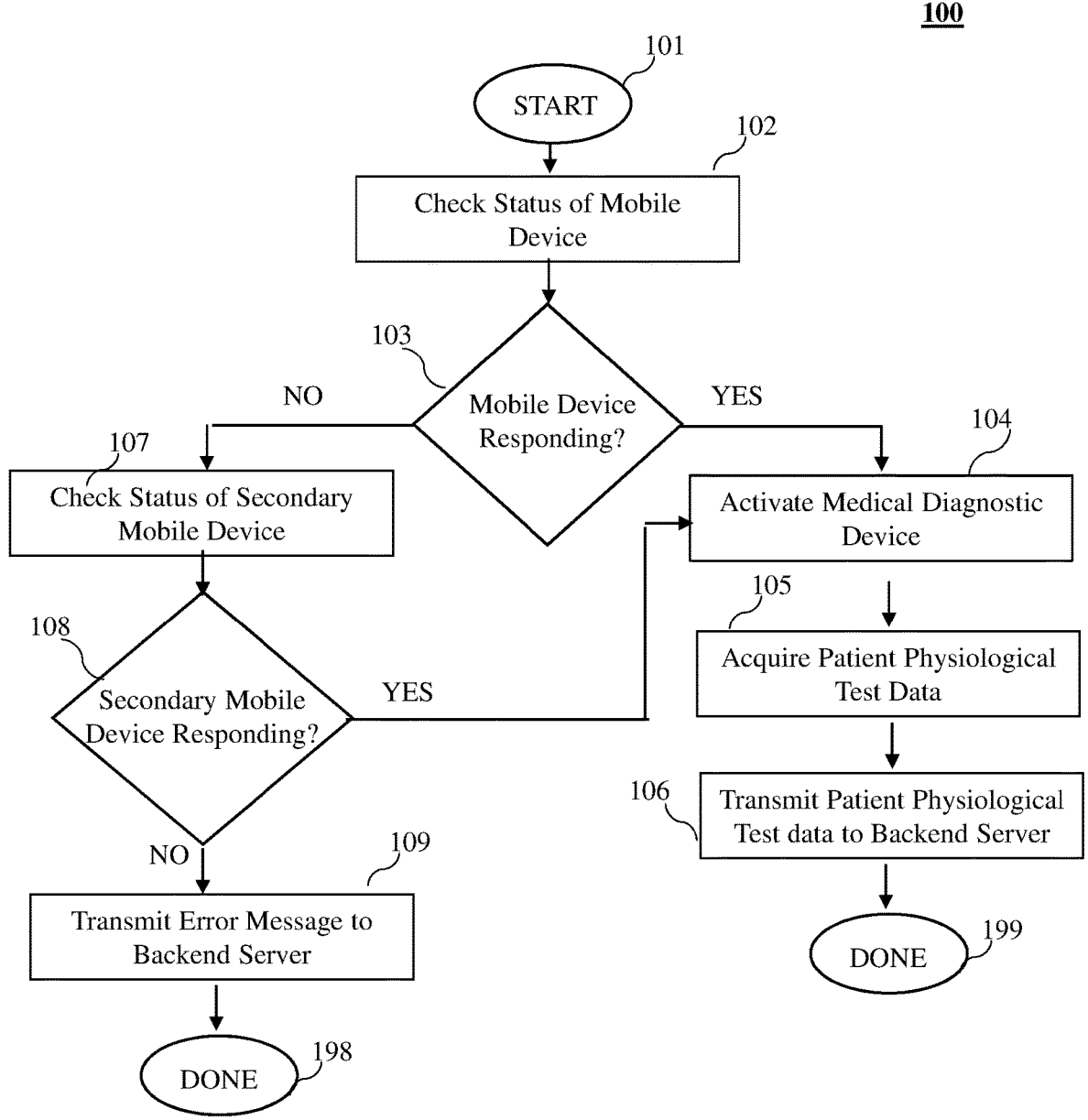
FIG. 1 is a Flow Diagram of RPM APP—Primary RPM Mobile Device Failure.

The present invention Smart Remote Patient Monitoring (SRPM) has a RPM—Primary RPM Mobile Device Failure flow diagram 100, which is illustrated in FIG. 1, wherein the status of the Mobile device is checked 102 to ensure proper operation. In the event that mobile device is responding 103, the medical diagnostic device is then activated 104. Next patient physiological parameters are acquired thru the medical diagnostic device 105. The patient physiological parameters are then wirelessly transmitted to the backend server for the healthcare provider viewing thru the use of the RPM Physician Portal 106 and the testing process is completed 199. In the event that the primary mobile device does not respond, the status of the secondary mobile device is then checked 107. If the secondary mobile device does not respond either 108, an error message is transmitted to the backend server 109 and the testing process is completed 198. In the event that secondary mobile device does respond properly, the medical diagnostic device is then activated 104. Next patient physiological parameters are acquired thru the medical diagnostic device 105. The patient physiological parameters are then wirelessly transmitted to the backend server for the healthcare provider viewing thru the use of the RPM Physician Portal 106 and the testing process is completed 199.

Figure 2:
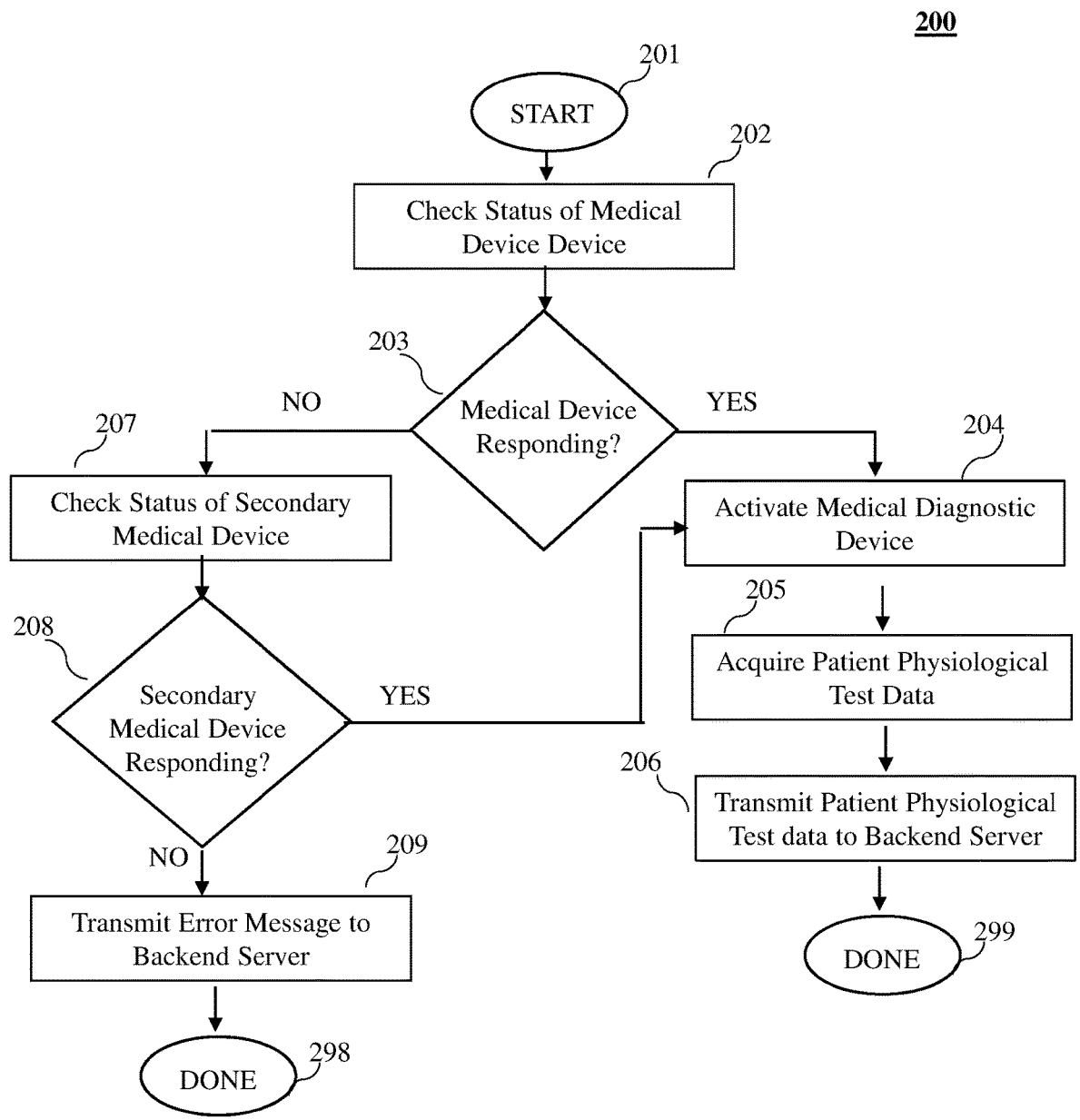
FIG. 2 is a Flow Diagram of RPM APP—Primary Medical Device Failure.

The present invention Smart Remote Patient Monitoring (SRPM) has a RPM—Primary Medical Device Failure flow diagram 200, which is illustrated in FIG. 2, wherein the status of the medical device is checked 202 to ensure proper operation. In the event that Medical device is responding 203, the medical diagnostic device is then activated 204. Next patient physiological parameters are acquired thru the medical diagnostic device 205. The patient physiological parameters are then wirelessly transmitted to the backend server for the healthcare provider viewing thru the use of the RPM Physician Portal 206 and the testing process is completed 299. In the event that the primary medical Device does not respond, the status of the secondary medical device is then checked 207. If the secondary medical device does not respond either 208, an error message is transmitted to the backend server 209 and the testing process is completed 298. In the event that secondary medical device does respond properly, the medical diagnostic device is then activated 204. Next patient physiological parameters are acquired thru the medical diagnostic device 205. The patient physiological parameters are then wirelessly transmitted to the backend server for the healthcare provider viewing thru the use of the RPM Physician Portal 206 and the testing process is completed 299.

Figure 3:
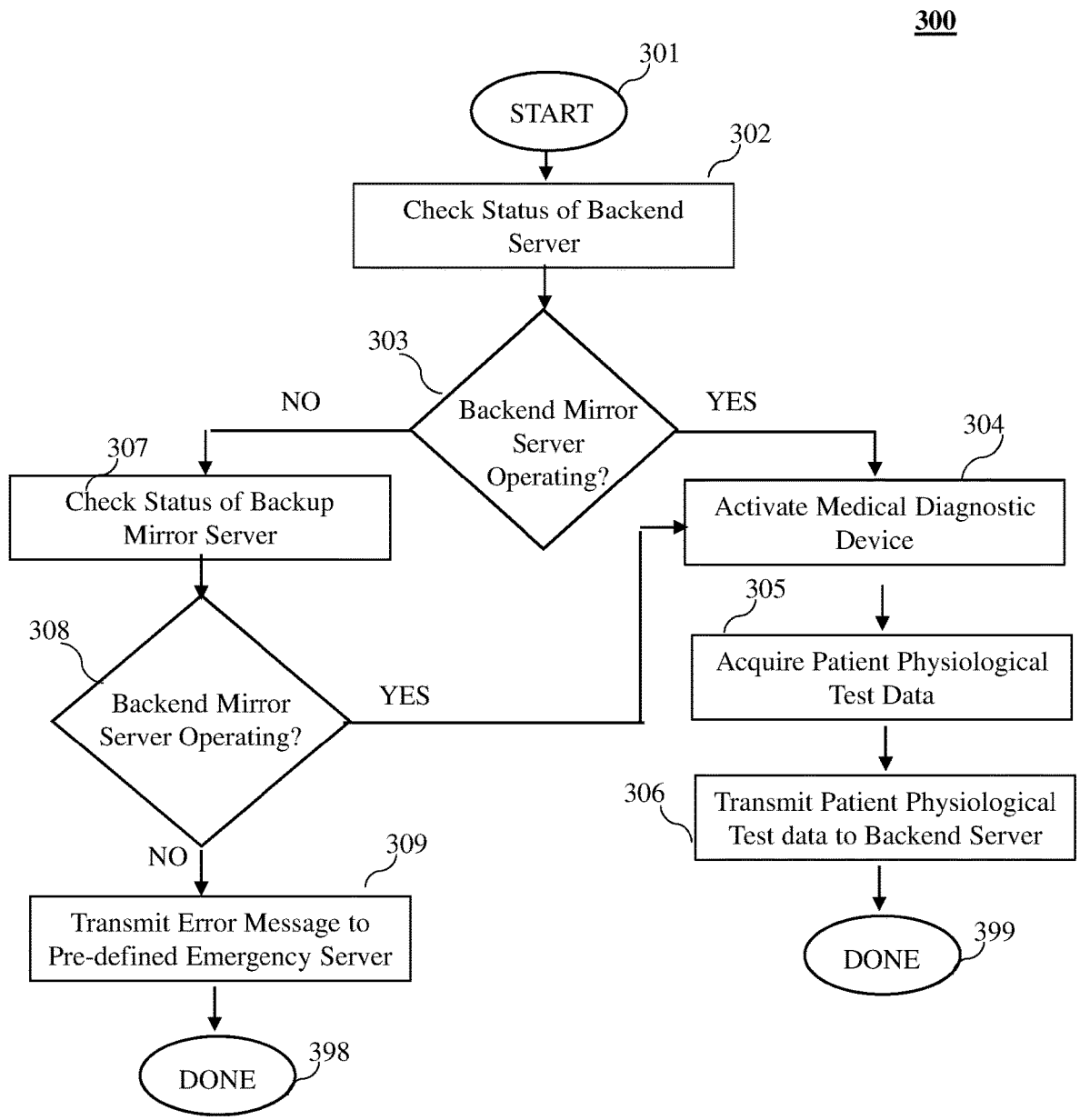
FIG. 3 is a Flow Diagram of RPM Backend Server—Primary Backend Server Failure.

The present invention Smart Remote Patient Monitoring (SRPM) has a RPM—Primary Backend Server Failure flow diagram 300, which is illustrated in FIG. 3, wherein the status of the backend server is checked 302 to ensure proper operation. In the event that backend server is responding 303, the medical diagnostic device is then activated 304. Next patient physiological parameters are acquired thru the medical diagnostic device 305. The patient physiological parameters are then wirelessly transmitted to the backend server for the healthcare provider viewing thru the use of the RPM Physician Portal 306 and the testing process is completed 399. In the event that the primary backend server does not respond, the status of the secondary backup mirror server is then checked 307. If the secondary backup mirror server does not respond either 308, an error message is transmitted to a predefined emergency server 309 and the testing process is completed 398. In the event that secondary backup mirror does respond properly, the medical diagnostic device is then activated 304. Next patient physiological parameters are acquired thru the medical diagnostic device 305. The patient physiological parameters are then wirelessly transmitted to the backend server for the healthcare provider viewing thru the use of the RPM Physician Portal 306 and the testing process is completed 399.

Figure 4:
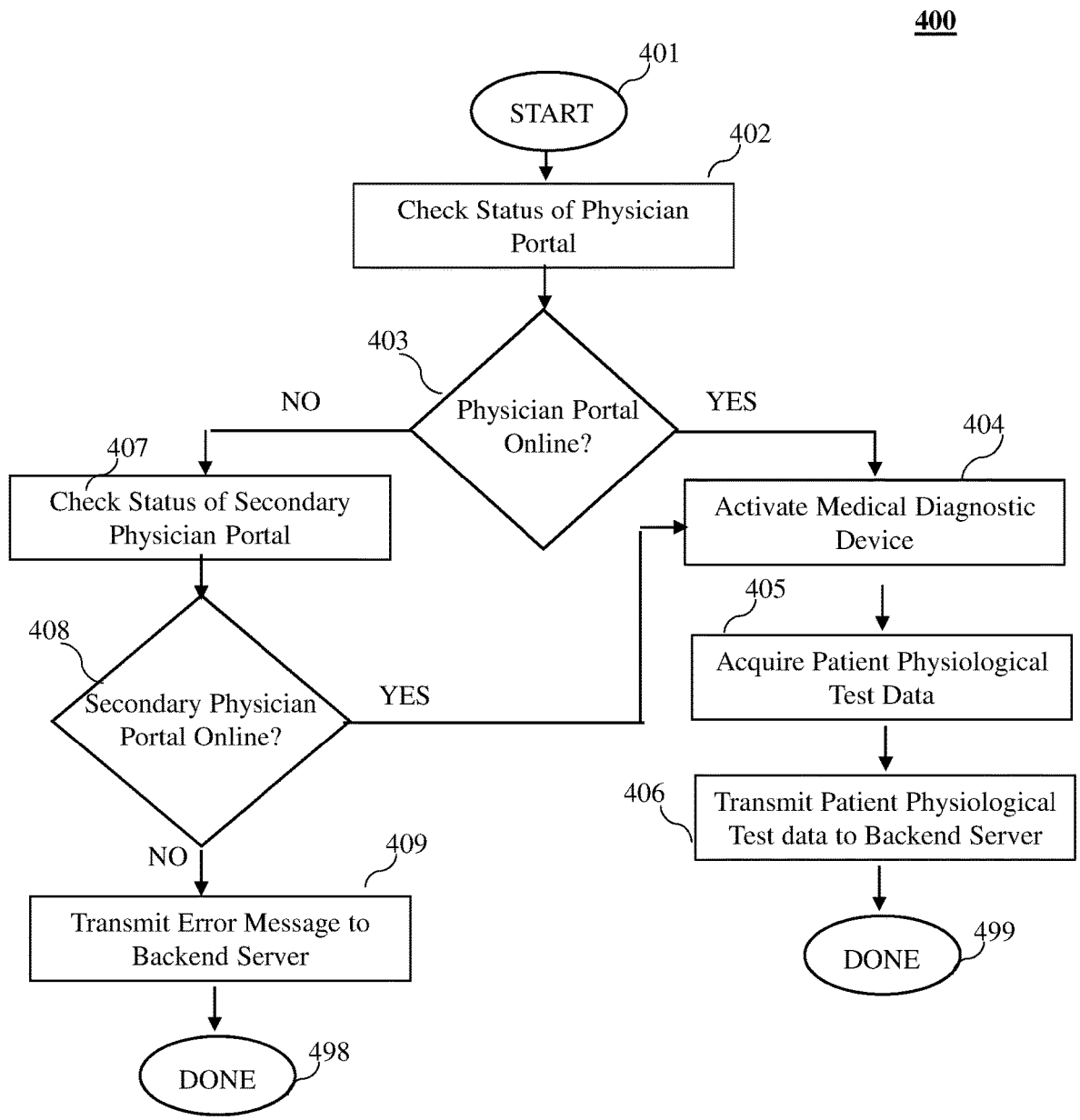
FIG. 4 is a Flow Diagram of RPM Physician Portal—Primary Physician Portal Failure.

The present invention Smart Remote Patient Monitoring (SRPM) has a RPM—Primary Physician Portal Failure flow diagram 400, which is illustrated in FIG. 4, wherein the status of the primary physician portal is checked 402 to ensure proper operation. In the event that primary physician portal is responding 403, the medical diagnostic device is then activated 404. Next patient physiological parameters are acquired thru the medical diagnostic device 405. The patient physiological parameters are then wirelessly transmitted to the backend server for the healthcare provider viewing thru the use of the RPM Physician Portal 406 and the testing process is completed 499. In the event that the primary physician portal does not respond, the status of the secondary physician portal is then checked 407. If the secondary physician portal does not respond either 408, an error message is transmitted to the backend server 409 and the testing process is completed 498. In the event that secondary physician portal does respond properly, the medical diagnostic device is then activated 404. Next patient physiological parameters are acquired thru the medical diagnostic device 405. The patient physiological parameters are then wirelessly transmitted to the backend server for the healthcare provider viewing thru the use of the RPM Physician Portal 406 and the testing process is completed 499.

Figure 5:
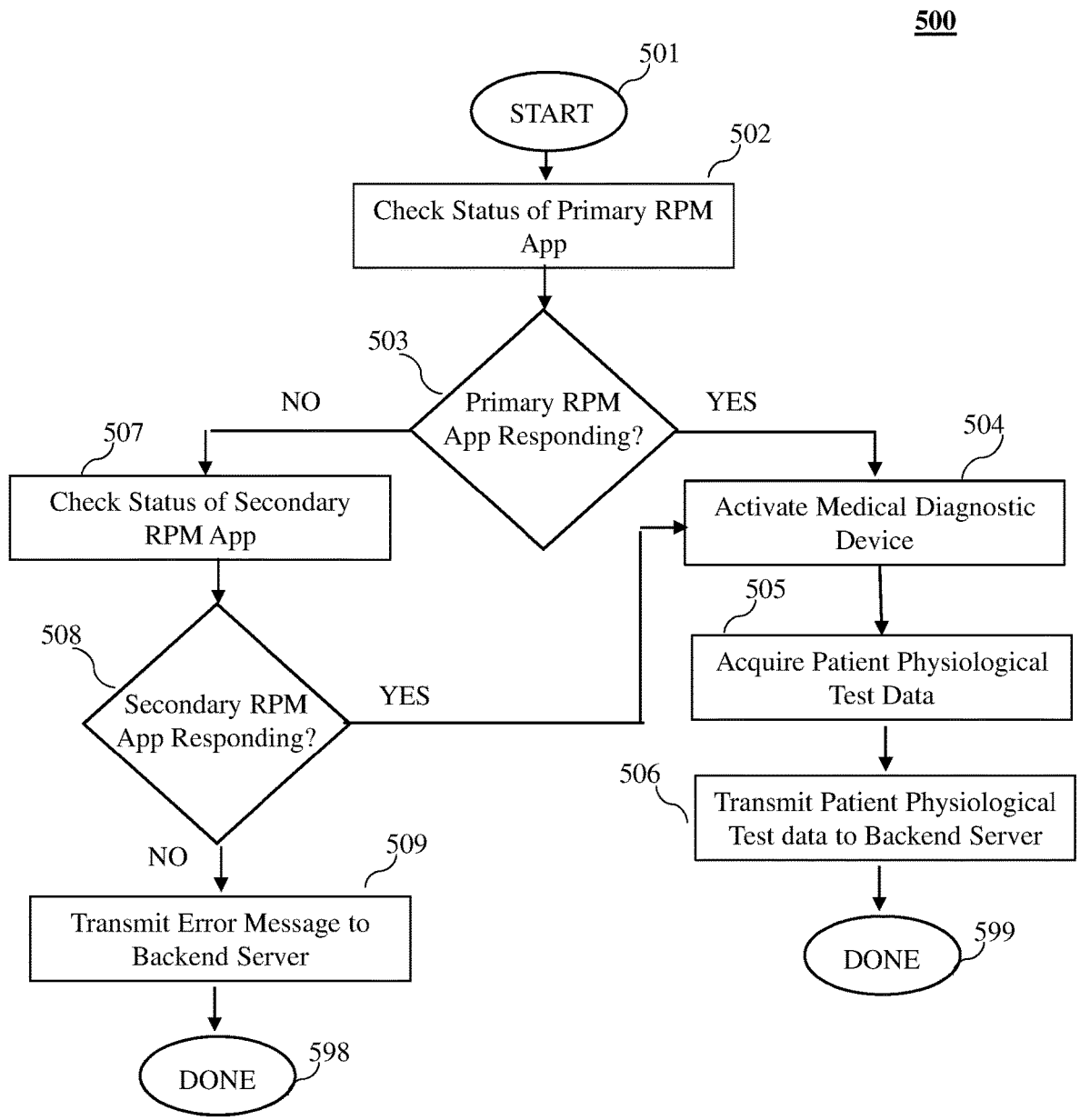
FIG. 5 is a Flow Diagram of RPM APP—Primary RPM App Failure.

The present invention Smart Remote Patient Monitoring (SRPM) has a RPM—Primary RPM App Failure flow diagram 500, which is illustrated in FIG. 5, wherein the status of the primary RPM App is checked 502 to ensure proper operation. In the event that primary RPM App is responding 503, the medical diagnostic device is then activated 504. Next patient physiological parameters are acquired thru the medical diagnostic device 505. The patient physiological parameters are then wirelessly transmitted to the backend server for the healthcare provider viewing thru the use of the RPM Physician Portal 506 and the testing process is completed 599. In the event that the primary RPM App does not respond, the status of the secondary RPM App is then checked 507. If the secondary RPM App does not respond either 508, an error message is transmitted to the backend server 509 and the testing process is completed 598. In the event that secondary RPM App does respond properly, the medical diagnostic device is then activated 504. Next patient physiological parameters are acquired thru the medical diagnostic device 505. The patient physiological parameters are then wirelessly transmitted to the backend server for the healthcare provider viewing thru the use of the RPM Physician Portal 506 and the testing process is completed 599.

Figure 6:
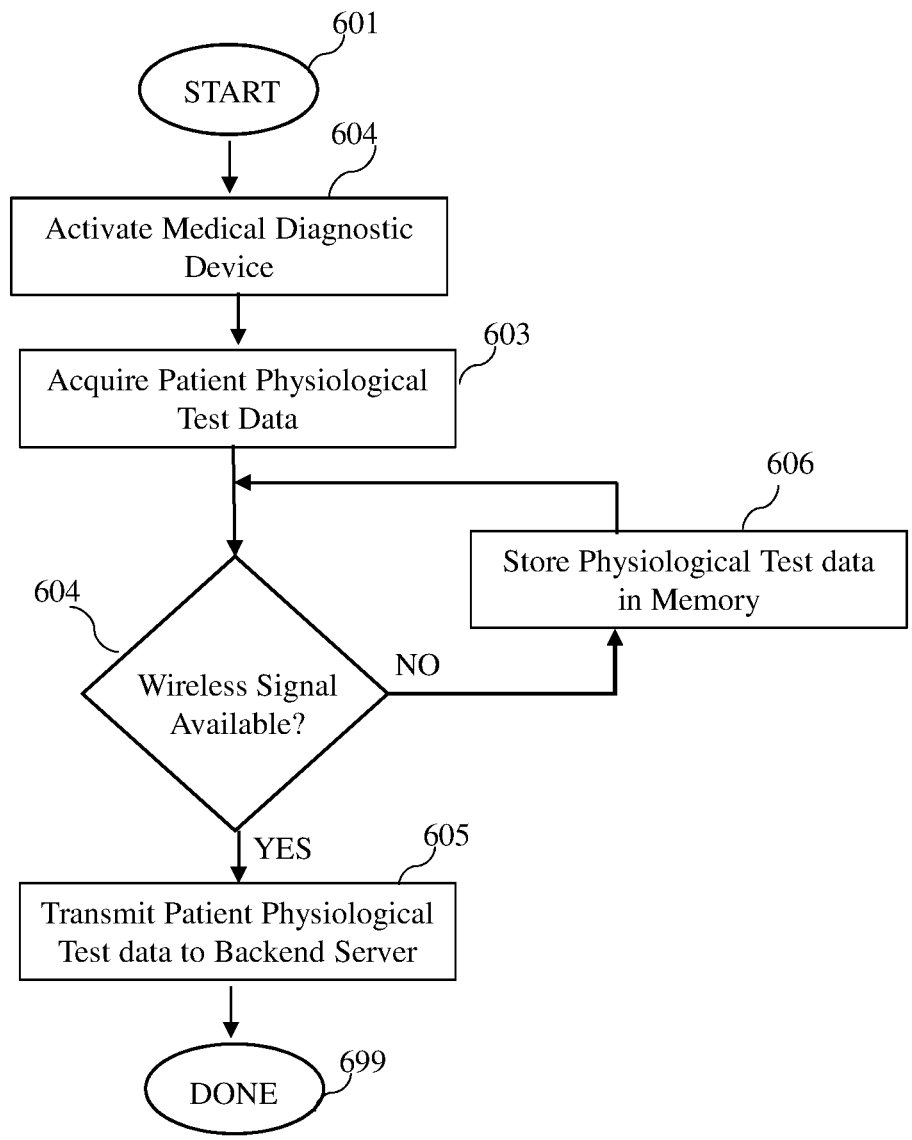
FIG. 6 is a Flow Diagram of RPM APP—Delayed Wireless Transmission.

The present invention Smart Remote Patient Monitoring (SRPM) has a RPM—Delayed Wireless Transmission flow diagram 600, which is illustrated in FIG. 6, wherein the medical diagnostic device is activated 602. Next patient physiological parameters are acquired thru the medical diagnostic device 603. Next, the status of the wireless communication signal is checked 604. In the event that Wireless Signal is not available, the physiological parameters are then stored in the mobile device's non-volatile memory 606 and the status of the wireless signal is checked again 604. Once wireless signal becomes available, the patient physiological parameters are then transmitted to the backend server for the healthcare provider viewing thru the use of the RPM Physician Portal 605 and the testing process is completed 699.

Figure 7:
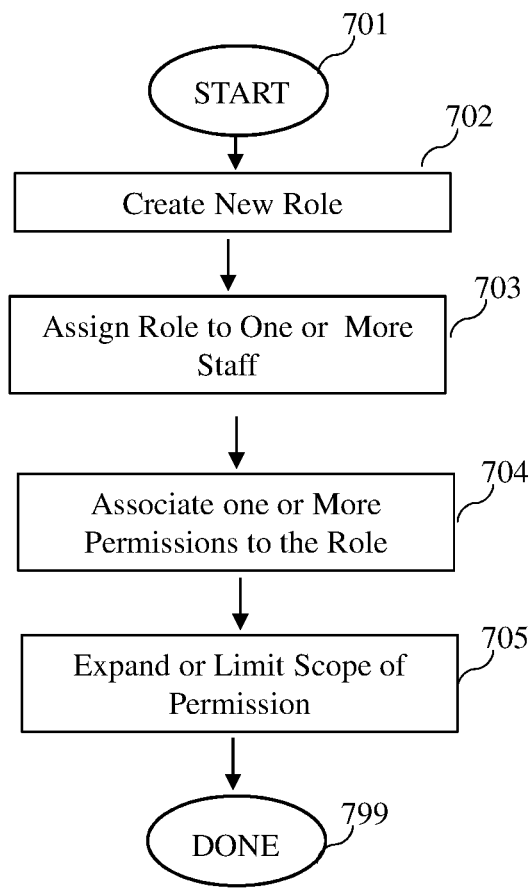
FIG. 7 is a Flow Diagram of RPM Physician Portal—Multi-Layer Permission and Role Assignment.

The present invention Smart Remote Patient Monitoring (SRPM) has a RPM Physician Portal—Multi-Layer Permission and Role Assignment flow diagram 700, which is illustrated in FIG. 7, wherein one or more Roles are created 702 using the Physician Portal of the SRPM. Next, the created roles are assigned to one or more staff member 703. Following that, one or more permissions are associated with each role that was created 704. Finally, the scope of each permission is expanded or limited 705 and the role permission assignment process is completed 799.

Figure 8:
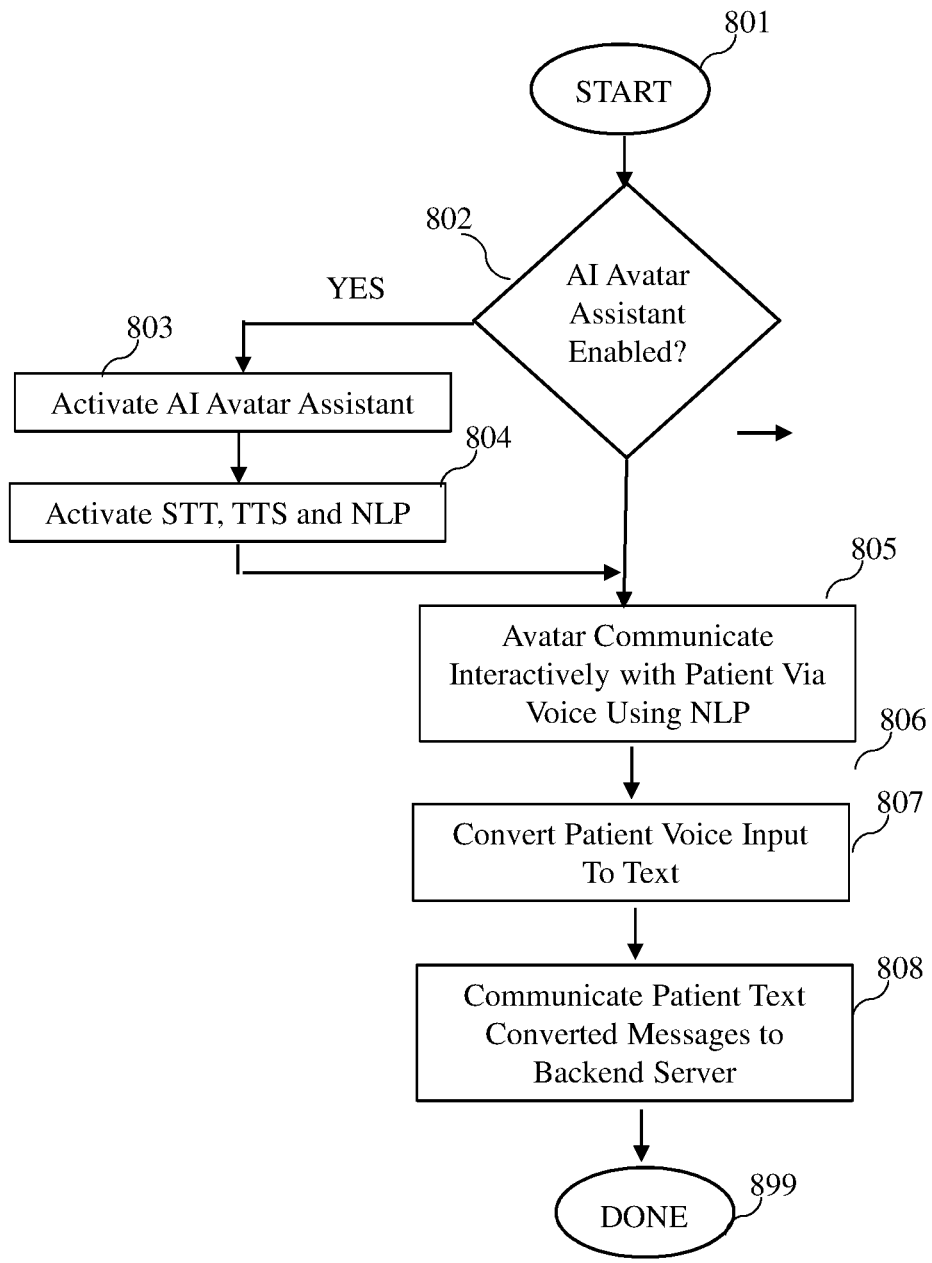
FIG. 8 is a Flow Diagram of RPM Physician Portal—Artificial Intelligence Avatar Virtual Assistant.

The present invention Smart Remote Patient Monitoring (SRPM) has a RPM App and Physician Portal—Artificial Intelligence (AI) Avatar Virtual Assistant flow diagram 800, which is illustrated in FIG. 8, wherein the status of AI Avatar Virtual Assistant is checked. If AI Avatar Virtual Assistant is enabled, then AI Avatar Virtual Assistant is activated 803 and Speech To Text (STT), Text To Speech (TTS) and Natural Language Processing features are all enabled 804. Next, the microphone and speaker of the tablet or mobile device is utilized for a two-way voice communication. Following that, the AI Avatar Virtual Assistant utilizes STT, TTS and NLP to manage interactive voice communication with the patient 805. The patient voice communications are then converted to text data utilizing STT technology 807 and the converted text information s sent wirelessly to the backend server for the healthcare provider to access thru the physician portal 808 and the AI Avatar Virtual Assistant process is then completed 899.

Figure 9:
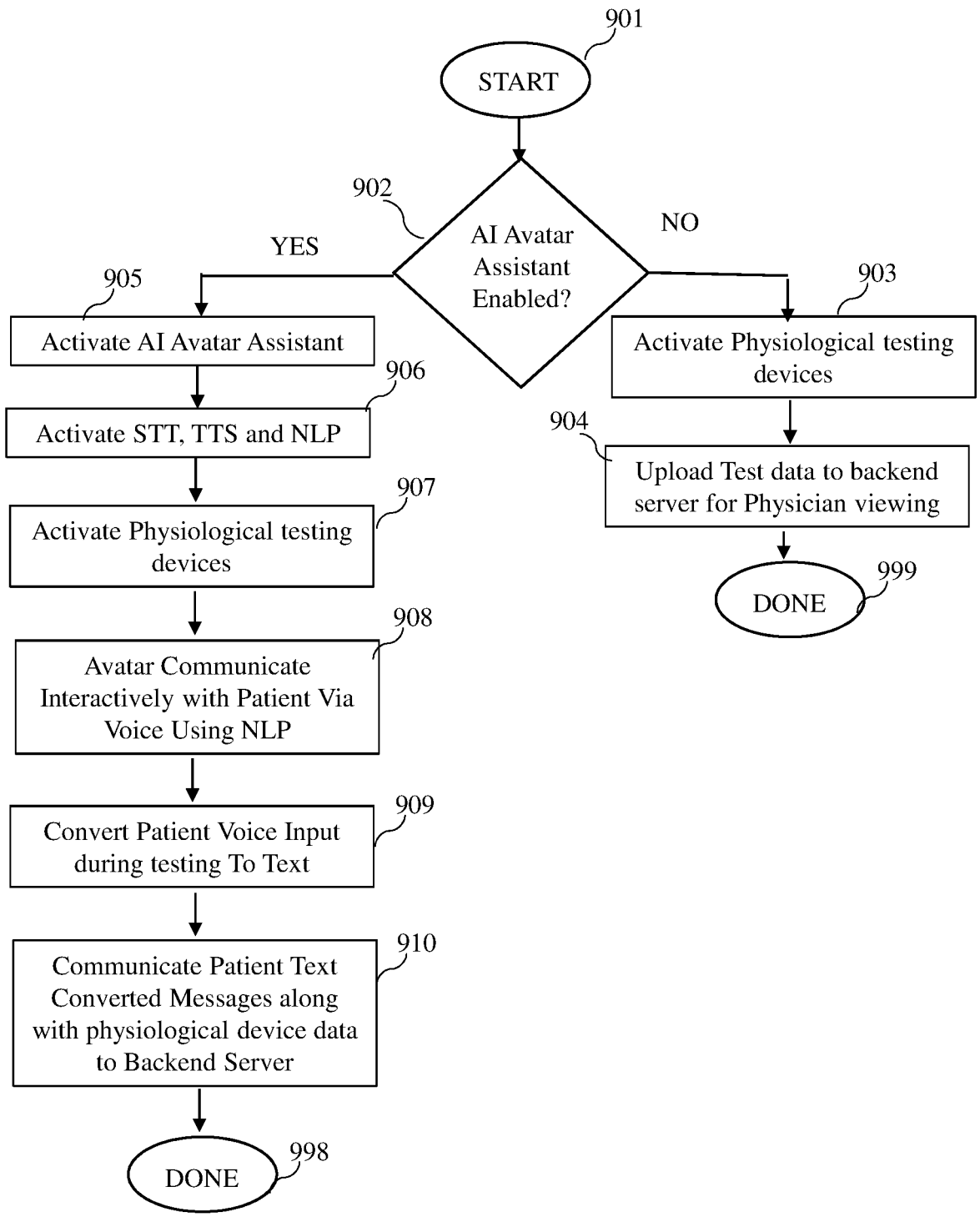
FIG. 9 is a Flow Diagram of RPM APP—Artificial Intelligence Avatar Virtual Assistant Multi-Dimensional Testing Process.

The present invention Smart Remote Patient Monitoring (SRPM) has a RPM—Artificial Intelligence (AI) Avatar Virtual Assistant Multi-Dimensional Testing Process flow diagram 900, which is illustrated in FIG. 9, wherein the status of AI Avatar Virtual Assistant is checked 902. If AI Avatar Virtual Assistant is not enabled, then physiological testing devices are activated 903 and the acquired test data is uploaded to the backend server for physician viewing thru the physician portal 904 and The process is then complete 999. In the event that AI Avatar Virtual Assistant is enabled, then the AI Avatar Assist is activated 905, and Speech To Text (STT), Text To Speech (TTS) and Natural Language Processing features are all enabled 906. Next, the physiological testing devices are activated 907. Following that, the AI Avatar Virtual Assistant participates in interactive two-way voice communication with the patient, to collect voice inputs from the patient on his or her condition and state of well-being prior to, during and after the testing process 908. The acquired voice inputs from the patient is then converted to Text data using Speech To Text (STT) technology 909. The converted text data is then uploaded to the backend server along with the acquired physiological parameters from medical equipment 910. This novel concept provides an additional depth and layer to patient's physiological parameters from the devices but enabling the healthcare providers to monitor patient's well-being and state of mind during the entire testing process. The process is then complete 998.

Figure 10:
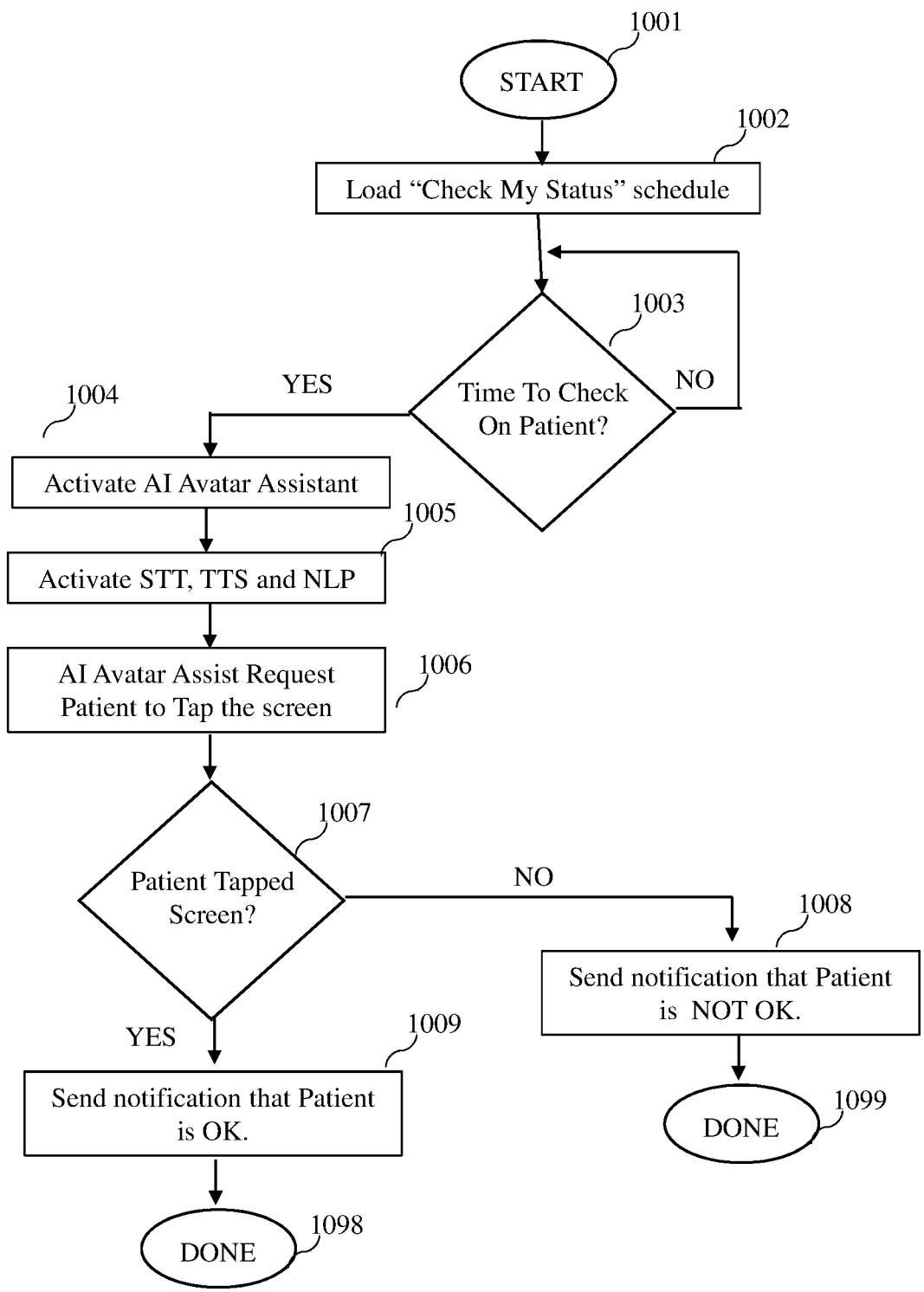
FIG. 10 is a Flow Diagram of RPM APP—Check My Status, Artificial Intelligence Avatar Virtual Assistant Passive Monitoring Process.

The present invention Smart Remote Patient Monitoring (SRPM) has a RPM—Artificial Intelligence Avatar Virtual Assistant "Check My Status" Process flow diagram 1000, which is illustrated in FIG. 10, wherein the "Check My Status" schedule is loaded and enabled 1002. Next the schedule time for checking on the patient is examined 1003. In the event that it is time to check on patient AI Avatar Virtual Assistant is activated 1004 and Speech To Text (STT), Text To Speech (TTS) and Natural Language Processing features are all enabled 1005. Next, a reminder message is displayed on screen along with AI Avatar Virtual Assistant voice announcement for the patient to tap the screen 1006. Following that, a check is made to determine if the patient has tapped the screen within the pre-determined allowable time period 1007. In the event the patient has successfully tapped the screen within the allowable time period, then a notification is sent out indicating patient is OK 1009 and the process is complete 1098. In the event however that the patient has not successfully tapped the screen within the allowable time period, then a notification is sent out indicating the patient is not OK 1008 and the process is complete 1099.

Figure 11:
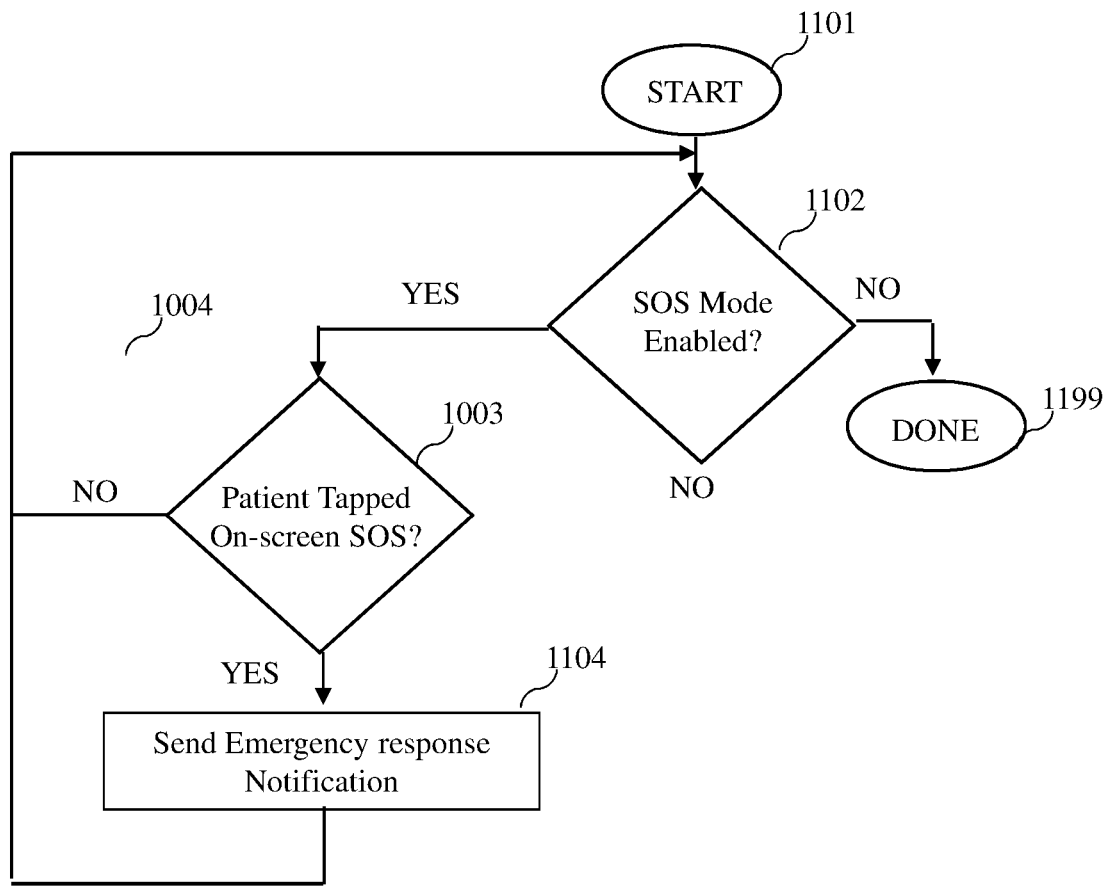
FIG. 11 is a Flow Diagram of RPM APP—One-touch On-screen Emergency Response Button Process.

The present invention Smart Remote Patient Monitoring (SRPM) has a RPM—One-touch On-screen Emergency Response (SOS) Button Process flow diagram 1100, which is illustrated in FIG. 11, wherein a check is made to see if SOS mode is enabled 1102. If the SOS is not enabled, then the process is complete 1199. In the event that SOS mode is enabled, check is then made to see if the patient has touched the screen to activate the SOS Alert button 1003. If the patient has not touched the on-screen SOS button to initiate an alert, then the process continues in a loop to check if SOS mode is still enabled 1102. In the event that the patient touches the on-screen SOS button on tablet or mobile device screen, an alert emergency response notification is then sent out 1104.

Figure 12:
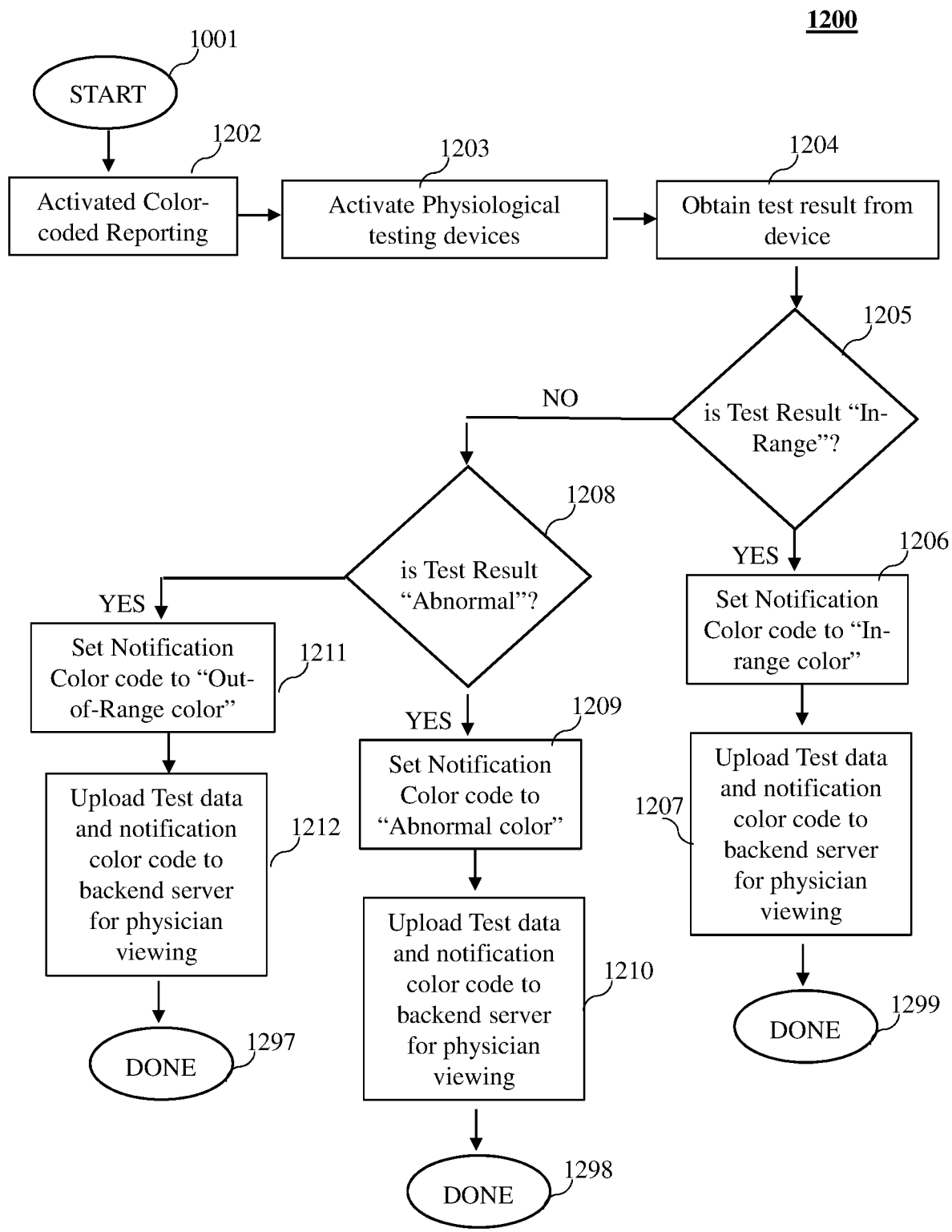
FIG. 12 is a Flow Diagram of RPM APP—Out of Range Test Results Color-Coded reporting to backend server and physician portal.

The present invention Smart Remote Patient Monitoring (SRPM) has a RPM—Out of Range Test Results Color-Coded notification reporting to backend server and physician portal Process flow diagram 1200, which is illustrated in FIG. 12, wherein color-coded notification reporting is enabled 1202. Next, physiological testing devices are activated 1203 and the patient test data is acquired 1204. Following that, physiological parameters are examined to ensure the test result is within allowable range 1205. In the event that the physiological device test data is in-range, color-coded notification is set to "in-range" color status 1206 and the test data along with color-coded notification are uploaded to the backend server to be viewed by the healthcare provider thru the physician portal 1207 and the process is complete 1299. In the event that the physiological device test data is not "in-range", then physiological parameters are examined to determine if the test result is within "abnormal" range 1208. In the event that the physiological device test data is within abnormal range, then color-coded notification is set to "abnormal range" color status 1209 and the test data along with color-coded notification are uploaded to the backend server to be viewed by the healthcare provider thru the physician portal 1210 and the process is complete 1298. In the event that the physiological device test data is not "abnormal", then color-coded notification is set to "Out-of-range" color status 1211 and the test data along with color-coded notification are uploaded to the backend server to be viewed by the healthcare provider thru the physician portal 1212 and the process is complete 1297.

Figure 13:
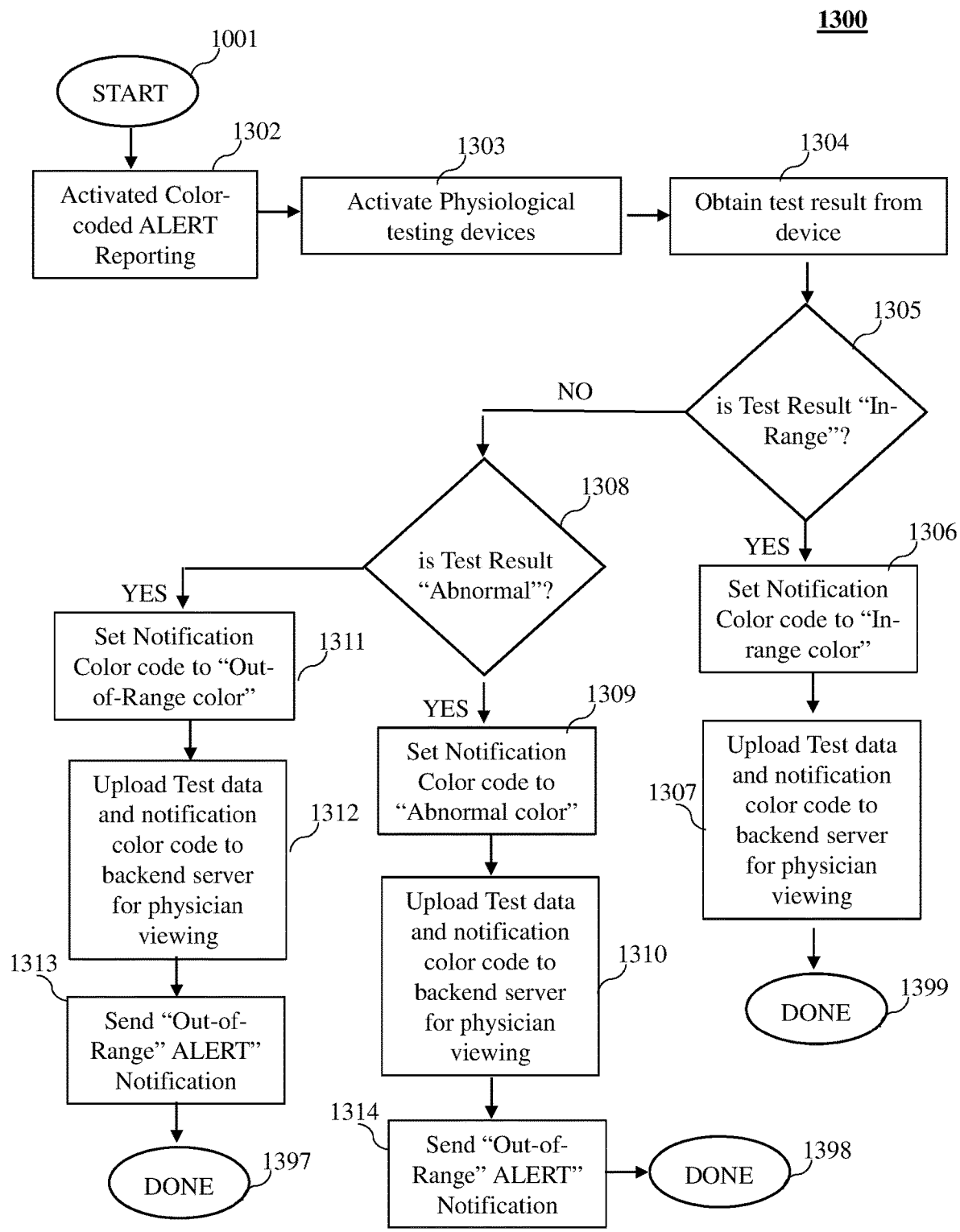
FIG. 13 is a Flow Diagram of RPM APP—Out of Range Test Results Color-Coded reporting with Multiple ALERT Notification Process.

The present invention Smart Remote Patient Monitoring (SRPM) has a RPM—Out of Range Test Results Color-Coded notification and ALERT reporting to backend server and physician portal Process flow diagram 1300, which is illustrated in FIG. 13, wherein color-coded notification and ALERT reporting is enabled 1302. Next, physiological testing devices are activated 1303 and the patient test data is acquired 1304. Following that, physiological parameters are examined to ensure the test result is within allowable range 1305. In the event that the physiological device test data is in-range, color-coded notification is set to "in-range" color status 1306 and the test data along with color-coded notification are uploaded to the backend server to be viewed by the healthcare provider thru the physician portal 1307 and the process is complete 1399. In the event that the physiological device test data is not "in-range", then physiological parameters are examined to determine if the test result is within "abnormal" range 1308. In the event that the physiological device test data is within abnormal range, then color-coded notification is set to "abnormal range" color status 1309 and the test data along with color-coded notification are uploaded to the backend server to be viewed by the healthcare provider thru the physician portal 1310. Next "abnormal" ALERT notification is sent out 1314 and the process is complete 1398. In the event that the physiological device test data is not "abnormal", then color-coded notification is set to "Out-of-range" color status 1311 and the test data along with color-coded notification are uploaded to the backend server to be viewed by the healthcare provider thru the physician portal 1312. Next "Out-of-range" ALERT notification is sent out 1313 and the process is complete 1297

Figure 14:
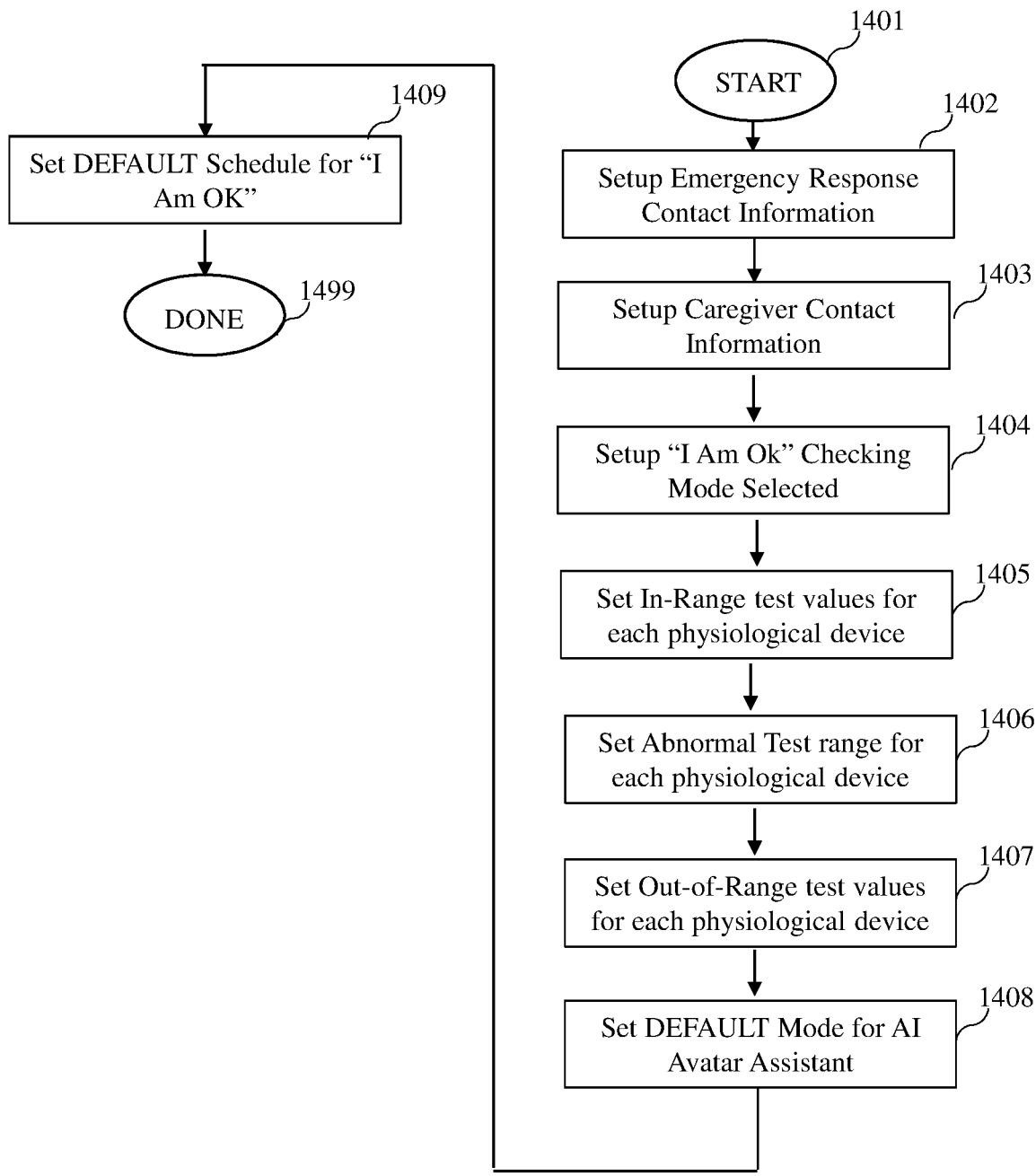
FIG. 14 is a Flow Diagram of RPM APP—Initial Setup Process.

The present invention Smart Remote Patient Monitoring (SRPM) has a RPM—Initial Setup Process flow diagram 1400, which is illustrated in FIG. 14, wherein Emergency Response Contact information is entered into patient profile 1402. Next, Caregiver contact information is entered into patient profile 1403. Following that, "Check My Status" checking mode is selected 1404. Next the "In-range" test values for each of the physiological medical equipment are entered into patient 1405. Following that, the "abnormal range" test values for each of the physiological test devices are entered into patient 1406. Next the "Out-of-range" test values for each of the physiological test devices are entered into patient profile 1407. Following that, the DEFAULT mode for AI Avatar Virtual Assistant is selected 1408. Finally, the DEFAULT schedule for "CHECK MY STATUS" checking along with the patient response time period is inputted 1409 and the process is completed 1499.

Figure 15:
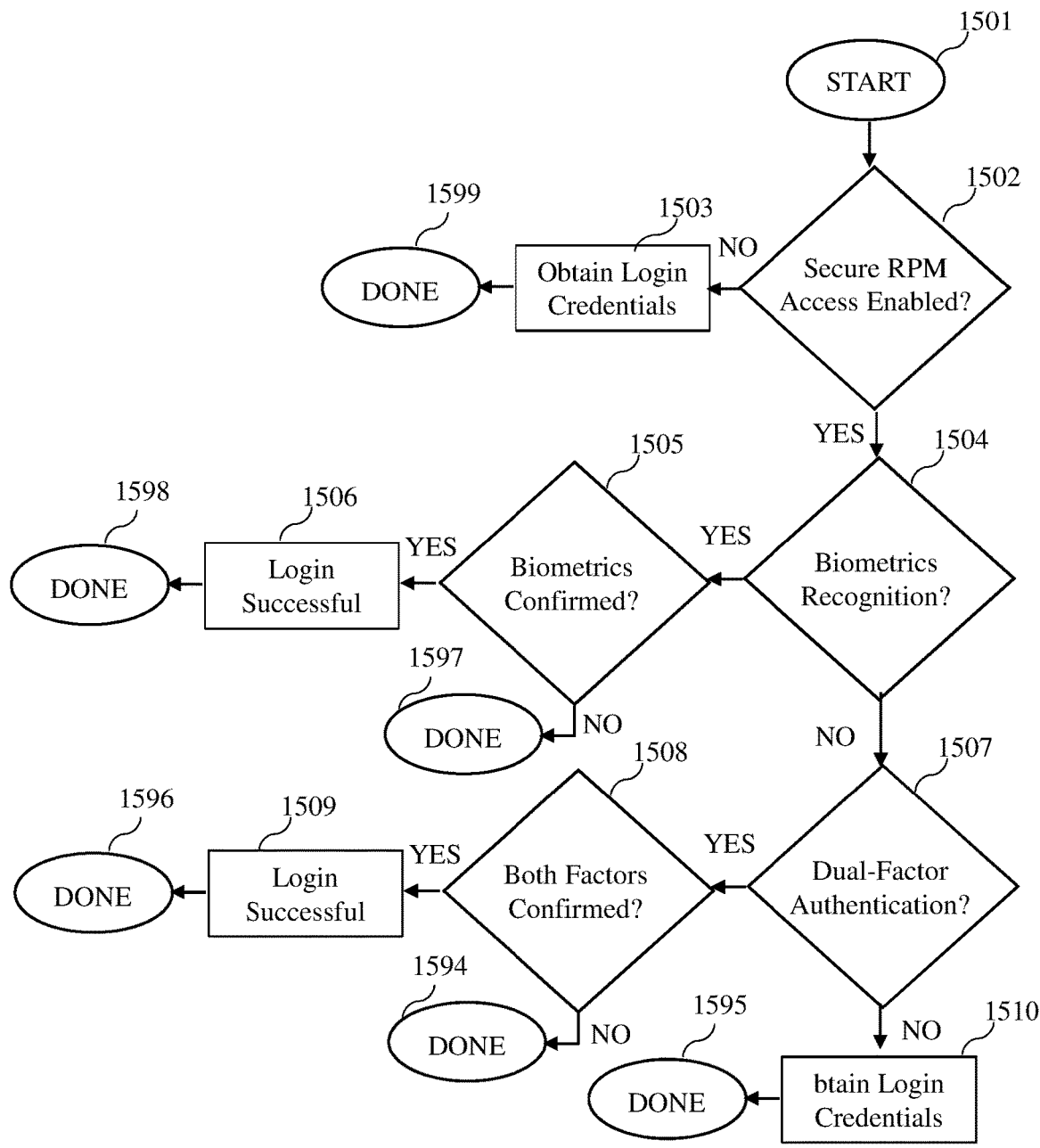
FIG. 15 is a Flow Diagram of RPM APP—Secure Remote Patient Monitoring Access.

The present invention Smart Remote Patient Monitoring (SRPM) has a RPM—Secure Remote Patient Monitoring Access Process flow diagram 1500, which is illustrated in FIG. 15, wherein a check is made to determine if the secure RPM access is enabled 1502. If secure RPM access mode is not selected, then patient Username and Password is obtained for standard login 1503 and the process is complete 1599. In the event that Secure RPM access is enabled, a check is made to see if biometric login is selected 1504. If biometrics login is selected, then patient biometrics is acquired and validated 1505. Patient biometrics may comprise of facial recognition, fingerprint scan, retina scan and voice recognition. In the event that patient biometrics are recognized and validated, patient is securely logged into the secure RPM for access 1506 and the process is complete 1598. IN the event that biometrics are not confirmed, the process is complete and patient is not logged in 1597. In the event that biometric security is not selected, a check is made to determine if Dual-factor Authenticating is selected 1507. In the event that Dual-factor authentication is selected, a check is made to ensure both authentication factors are validated 1508. In the event that both authentication factors are validated, the patient is securely logged into Secure RPM for access 1509 and the process is complete 1596. In the event that both authentication factors do not get validated, then the patient is not logged and the process is complete 1594. In the event that Dual-factor authentication is not selected, then then patient Username and Password is obtained for standard login 1510 and the process is complete 1595.

Figure 16:
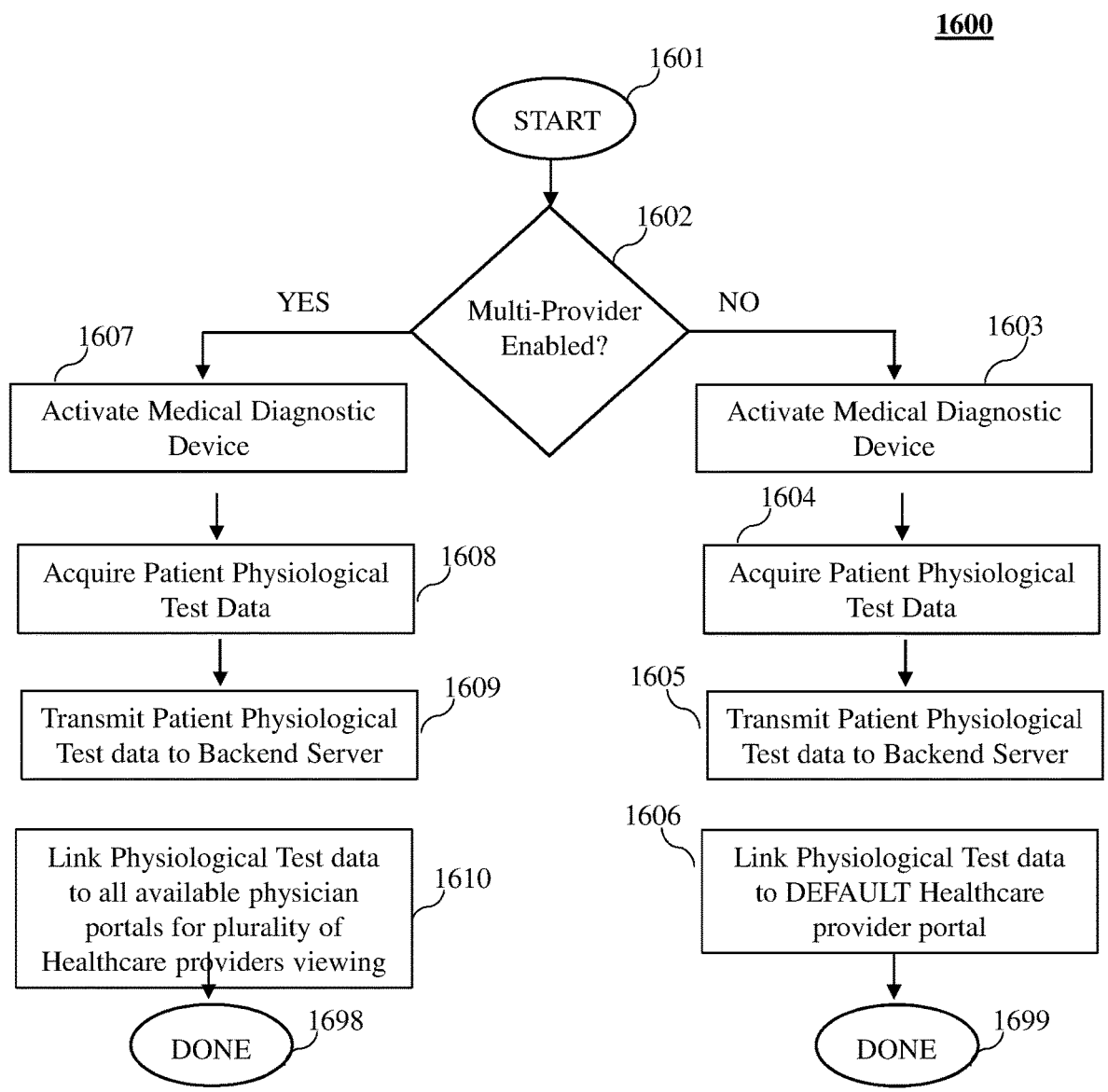
FIG. 16 is a Flow Diagram of RPM APP—Multi-healthcare provider Remote Patient Monitoring Process.

The present invention Smart Remote Patient Monitoring (SRPM) has a RPM—Multi-healthcare provider Remote Patient Monitoring Process flow diagram 1600, which is illustrated in FIG. 16, wherein a check is made to determine if the Multi-provider mode is enabled 1602. In the event that Multi-provider mode is not enabled, one or more physiological test devices are activated 1603. The patient test data is then acquired from the device 1604 and uploaded into the backend server 1605. The physiological parameters are then linked to the DEFAULT physician portal for the healthcare provider viewing 1606 and the process is complete 1699. In the event that Multi-provider mode is enabled, one or more physiological test devices are activated 1607. The patient test data is then acquired from the device 1608 and uploaded into the backend server 1609. The physiological parameters are then linked to all available physician portals for plurality of Healthcare providers viewing 1610 and the process is complete 1698.

The invention claimed is:

1. A remote patient monitoring system comprising:
   an application (APP) residing on a tablet or mobile device, said APP receiving and collecting one or more patient physiological parameters of a patient;
   one or more remote monitoring medical devices for use at a patient location to monitor the patient;
   a remote server for wirelessly receiving the collected one or more patient physiological parameters;
   providing secure access of the remotely collected one or more patient physiological parameters to a healthcare provider through a web-based physicians portal;
   wherein the APP utilizes an Artificial Intelligence (AI) Avatar virtual assistant to:
      utilize Text To Speech (TTS) to interactively communicate with the patient via voice prior to, during, and after obtaining the one or more patient physiological parameters through the one or more remote monitoring medical devices;
      utilize Speech To Text (STT) to convert the patient's interactive voice conversation to text;
      utilize Natural Language Processing (NLP) to understand the interactive voice conversation;
      combine the patient text input with the obtained one or more patient physiological parameters,
      transfer the combined patient text input and the obtained one or more patient physiological parameters to a backend server;
      provide the healthcare provider access to the patient text input and one or more patient physiological parameters through the use of the web-based portal;
   provide a "Check My Status" passive monitoring system via the AI Avatar virtual assistant to:
      inquire about the patient's well-being based on a pre-determined schedule;
      require the patient to acknowledge their well-being and safety within a predetermined time period by touching the screen or speaking to the tablet or mobile device to confirm;
      utilize STT and NLP to digitize and analyze the patient acknowledgement; and
      send notifications to remote caregivers and healthcare providers informing them of the patient well-being status.

2. The remote patient monitoring system of claim 1, further comprising:
   a patient triage and symptom checker;
   utilizing the AI Avatar virtual assistant;
   utilizing STT, TTS and NLP;
   interactively communicating with the patient via voice, checking on patient symptoms and triaging the patient.

3. The remote patient monitoring system of claim 1, further comprising an emergency response (SOS) button on the tablet or mobile device screen, enabling the patient being monitored to touch or press the SOS button to send an ALERT notification to healthcare providers, caregivers and emergency first responders prior to, during and after the medical device testing process and physiological parameters acquisition.

4. The remote patient monitoring system of claim 1, further comprising software redundancies through enabling of an alternative mirroring application capable of automatically self-activating and managing the monitoring devices in the event the default application crashes or stops running.

5. The remote patient monitoring system of claim 1, further comprising a secure patient access by utilizing (a) biometrics authentication including facial recognition, fingerprint scanning, retina scanning and voice recognition, and (b) dual-factor authentication including the use of passwords, email authentication and secondary wireless authenticating devices such as wireless fob.

6. The remote patient monitoring system of claim 1, further comprising multiple web-based physician portals in parallel providing a plurality of healthcare providers simultaneous secure access to the remotely collected one or more patient physiological parameters.

7. The remote patient monitoring system of claim 1, further comprising a Personal Emergency Response System (PERS) device comprising a wireless portable device such as fob, enabling the patient to press and activate an SOS button on the PERS device to send an ALERT notifications to healthcare providers, caregivers and emergency first responders.

8. The remote patient monitoring system of claim 1, further comprising wearable devices including smart watches and smart wristbands to acquire patient vital signs and physiological parameters and wirelessly transmitting the acquired data to the backend server for healthcare provider access through the physician web portal.

9. The remote patient monitoring system of claim 1, further comprising a color-coded notification and alert system, performing the steps of analyzing the one or more patient physiological parameters obtained through the one or more remote monitoring medical devices, determining whether the one or more patient physiological parameters are within (a) a predetermined acceptable value, (b) a predetermined abnormal range value or (c) a predetermined out-of-range value, providing colorized notifications based on the status of the physiological parameters in respect to the above 3-level predetermined values, comprising a pre-determined color schemes for each of the above 3-level predetermined values, providing alert notifications to a plurality of recipients including healthcare providers, emergency first responders, caregivers and family members based on the status of the one or more patient physiological parameters in respect to the three levels of predetermined values.

* * * * *